(12) United States Patent
Murphy et al.

(10) Patent No.: US 10,631,877 B2
(45) Date of Patent: Apr. 28, 2020

(54) ORTHOGNATHIC BIOMECHANICAL SIMULATION

(71) Applicant: THE JOHNS HOPKINS UNIVERSITY, Baltimore, MD (US)

(72) Inventors: Ryan Murphy, Columbia, MD (US); Ehsan Basafa, Baltimore, MD (US); Mehran Armand, Fulton, MD (US); Chad Gordon, Lutherville, MD (US); Gerald Grant, Goshen, KY (US); Peter Liacouras, North Potomac, MD (US)

(73) Assignees: The Johns Hopkins University, Baltimore, MD (US); The United States of America, as represented by the Secretary of the Navy, Washington, DC (US); The United States of AMerica, as represented by the Secretary of the Defense, Washington, DC (US)

(*) Notice: Subject to any disclaimer, the term of this patent is extended or adjusted under 35 U.S.C. 154(b) by 149 days.

(21) Appl. No.: 15/100,241

(22) PCT Filed: Nov. 26, 2014

(86) PCT No.: PCT/US2014/067581
§ 371 (c)(1),
(2) Date: May 27, 2016

(87) PCT Pub. No.: WO2015/081177
PCT Pub. Date: Jun. 4, 2015

(65) Prior Publication Data
US 2017/0000565 A1 Jan. 5, 2017

Related U.S. Application Data

(60) Provisional application No. 62/049,866, filed on Sep. 12, 2014, provisional application No. 61/940,196,
(Continued)

(51) Int. Cl.
*A61B 17/15* (2006.01)
*G16H 50/50* (2018.01)
(Continued)

(52) U.S. Cl.
CPC .......... *A61B 17/15* (2013.01); *A61B 17/1695* (2013.01); *A61B 17/176* (2013.01);
(Continued)

(58) Field of Classification Search
None
See application file for complete search history.

(56) References Cited

U.S. PATENT DOCUMENTS 3,457,922 A 7/1969 Ray et al.
4,436,684 A 3/1984 White
(Continued)

FOREIGN PATENT DOCUMENTS

WO 2012147114 A1 11/2012
WO 2013101753 A1 7/2013

OTHER PUBLICATIONS

Molla; "General Principles of Bone Grafting in MAxillofacial Surgery"; Jan. 2001; The ORION vol. 8; https://pdfs.semanticscholar.org/ec2e/7ba90a8b9835e873687d9454a848842f26c4.pdf.*
(Continued)

*Primary Examiner* — Eddy Saint-Vil
*Assistant Examiner* — William D Ermlick
(74) *Attorney, Agent, or Firm* — MH2 Technology Law Group LLP

(57) ABSTRACT

Disclosed is a method of simulating mastication. The method includes obtaining computer-readable three-dimen-
(Continued)

sional representations of a first skeletal fragment including a portion of at least one of a mandible and a maxilla and of a recipient skeletal fragment including a portion of at least one of a mandible and a maxilla. The method also includes obtaining placement data and obtaining muscle insertion data. The method also includes simulating a contraction of a muscle positioned according to the muscle insertion data in a representation of a surgical hybrid comprising at least a portion of the first skeletal fragment positioned according to the placement data relative to at least a portion of the recipient skeletal fragment. The method also includes outputting a representation of mastication represented by the simulating.

12 Claims, 23 Drawing Sheets

Related U.S. Application Data filed on Feb. 14, 2014, provisional application No. 61/910,204, filed on Nov. 29, 2013.

(51) Int. Cl.
| | | |
|---|---|---|
| *A61B 17/17* | (2006.01) | |
| *G16H 20/40* | (2018.01) | |
| *A61B 34/10* | (2016.01) | |
| *A61B 34/20* | (2016.01) | |
| *A61B 17/16* | (2006.01) | |
| *A61B 17/80* | (2006.01) | |
| *A61F 2/28* | (2006.01) | |
| *G06F 19/00* | (2018.01) | |

(52) U.S. Cl.
CPC ...... *A61B 17/1739* (2013.01); *A61B 17/8085* (2013.01); *A61B 34/10* (2016.02); *A61B 34/20* (2016.02); *A61F 2/2803* (2013.01); *G06F 19/3481* (2013.01); *G16H 20/40* (2018.01); *G16H 50/50* (2018.01); *A61B 2034/105* (2016.02); *A61B 2034/108* (2016.02); *A61B 2034/2051* (2016.02); *A61B 2034/2055* (2016.02); *A61B 2034/2065* (2016.02); *Y02A 90/26* (2018.01)

(56) References Cited

U.S. PATENT DOCUMENTS

| | | | |
|---|---|---|---|
| 5,279,575 A | 1/1994 | Sugarbaker | |
| 5,741,215 A | 4/1998 | DUrso | |
| 5,810,712 A | 9/1998 | Dunn | |
| 5,951,498 A * | 9/1999 | Arnett | G06K 9/00281 600/587 |
| 6,079,681 A | 6/2000 | Stern et al. | |
| 6,112,109 A | 8/2000 | DUrso | |
| 6,120,290 A * | 9/2000 | Fukushima | A61C 11/00 433/54 |
| 6,226,548 B1 * | 5/2001 | Foley | A61B 17/7083 600/426 |
| 6,254,639 B1 | 7/2001 | Peckitt | |
| 6,285,902 B1 | 9/2001 | Kienzle, III et al. | |
| 6,491,699 B1 | 12/2002 | Henderson et al. | |
| 6,500,179 B1 | 12/2002 | Masini | |
| 6,608,628 B1 * | 8/2003 | Ross | G06T 17/20 345/619 |
| 6,726,678 B1 | 4/2004 | Nelson et al. | |
| 6,796,986 B2 | 9/2004 | Duffner | |
| 6,845,175 B2 * | 1/2005 | Kopelman | A61B 6/14 128/922 |
| 6,932,842 B1 | 8/2005 | Litschko et al. | |
| 7,050,877 B2 | 5/2006 | Iseki et al. | |
| 7,113,841 B2 | 9/2006 | Abe et al. | |
| 7,510,557 B1 | 3/2009 | Bonutti | |
| 7,596,399 B2 | 9/2009 | Singhal et al. | |
| 7,747,305 B2 | 6/2010 | Dean et al. | |
| 7,747,318 B2 | 6/2010 | John et al. | |
| 7,792,341 B2 * | 9/2010 | Schutyser | G06T 7/0012 382/128 |
| 7,857,821 B2 | 12/2010 | Couture et al. | |
| 7,953,260 B2 * | 5/2011 | Weinzweig | G06T 13/40 382/128 |
| 8,086,336 B2 | 12/2011 | Christensen | |
| 8,096,997 B2 | 1/2012 | Plaskos et al. | |
| 8,221,430 B2 * | 7/2012 | Park | A61B 5/055 606/88 |
| 8,221,461 B2 | 7/2012 | Kuiper et al. | |
| 8,357,165 B2 | 1/2013 | Grant et al. | |
| 8,397,732 B2 | 3/2013 | Singhal et al. | |
| 8,403,934 B2 | 3/2013 | Angibaud et al. | |
| 8,428,315 B2 * | 4/2013 | Suetens | G06T 19/20 382/128 |
| 8,518,085 B2 | 8/2013 | Winslow et al. | |
| 8,535,063 B1 | 9/2013 | Amato | |
| 8,650,005 B2 * | 2/2014 | Liao | G09B 23/283 703/1 |
| 8,706,285 B2 | 4/2014 | Narainasamy et al. | |
| 8,781,557 B2 | 7/2014 | Dean et al. | |
| 8,827,932 B2 * | 9/2014 | Hirabayashi | G06K 9/00214 600/587 |
| 9,208,558 B2 * | 12/2015 | Dean | G06T 7/0012 |
| 9,216,084 B2 | 12/2015 | Gordon et al. | |
| 9,330,206 B2 * | 5/2016 | Dean | G06T 19/00 |
| 9,659,152 B2 * | 5/2017 | Mueller | G06F 19/3437 |
| 2001/0021851 A1 | 9/2001 | Eberlein et al. | |
| 2002/0035458 A1 * | 3/2002 | Kim | G06T 15/00 703/6 |
| 2002/0165552 A1 | 11/2002 | Duffner | |
| 2004/0091845 A1 * | 5/2004 | Azerad | G09B 23/283 434/263 |
| 2004/0172044 A1 | 9/2004 | Grimm et al. | |
| 2004/0204760 A1 | 10/2004 | Fitz et al. | |
| 2005/0043835 A1 | 2/2005 | Christensen | |
| 2005/0113846 A1 | 5/2005 | Carson | |
| 2005/0117696 A1 * | 6/2005 | Suzuki | A61B 6/04 378/19 |
| 2006/0142657 A1 | 6/2006 | Quaid et al. | |
| 2006/0195111 A1 | 8/2006 | Couture | |
| 2007/0167701 A1 | 7/2007 | Sherman | |
| 2007/0207441 A1 | 9/2007 | Lauren | |
| 2008/0304725 A1 | 12/2008 | Leitner | |
| 2008/0306490 A1 | 12/2008 | Lakin et al. | |
| 2008/0319448 A1 * | 12/2008 | Lavallee | G06F 19/3437 606/102 |
| 2009/0088674 A1 | 4/2009 | Caillouette et al. | |
| 2009/0092948 A1 * | 4/2009 | Gantes | A61C 1/084 433/215 |
| 2009/0099570 A1 | 4/2009 | Paradis et al. | |
| 2009/0220122 A1 | 9/2009 | Richards et al. | |
| 2009/0240141 A1 | 9/2009 | Neubauer et al. | |
| 2009/0281623 A1 | 11/2009 | Kast et al. | |
| 2009/0311647 A1 * | 12/2009 | Fang | A61C 19/045 433/24 |
| 2010/0145425 A1 | 6/2010 | Jung et al. | |
| 2010/0145898 A1 | 6/2010 | Malfliet et al. | |
| 2010/0261998 A1 * | 10/2010 | Stiehl | A61B 19/50 600/424 |
| 2010/0311028 A1 * | 12/2010 | Bell, III | G09B 23/28 434/263 |
| 2011/0029093 A1 | 2/2011 | Bojarski et al. | |
| 2011/0066072 A1 | 3/2011 | Kawoos et al. | |
| 2011/0087465 A1 * | 4/2011 | Mahfouz | G06F 19/3437 703/1 |
| 2011/0102549 A1 * | 5/2011 | Takahashi | A61C 1/084 348/46 |
| 2011/0117530 A1 * | 5/2011 | Albocher | G16H 50/50 434/267 |
| 2011/0196377 A1 | 8/2011 | Hodorek et al. | |
| 2011/0208256 A1 | 8/2011 | Zuhars | |
| 2011/0244415 A1 | 10/2011 | Batesole | |

(56) References Cited

U.S. PATENT DOCUMENTS

| | | | |
|---|---|---|---|
| 2012/0041318 A1 | 2/2012 | Taylor | |
| 2012/0063655 A1 | 3/2012 | Dean et al. | |
| 2012/0109228 A1 | 5/2012 | Boyer et al. | |
| 2012/0259592 A1 | 10/2012 | Liao | |
| 2013/0035690 A1 | 2/2013 | Mittelstadt et al. | |
| 2013/0122463 A1* | 5/2013 | Csillag | A61C 8/0089 433/173 |
| 2013/0204600 A1* | 8/2013 | Mehra | G16H 50/50 703/11 |
| 2013/0211424 A1 | 8/2013 | Thiran et al. | |
| 2013/0211792 A1 | 8/2013 | Kang et al. | |
| 2013/0217996 A1* | 8/2013 | Finkelstein | A61B 5/1075 600/407 |
| 2013/0296872 A1 | 11/2013 | Davison et al. | |
| 2013/0297265 A1 | 11/2013 | Baloch et al. | |
| 2013/0310963 A1* | 11/2013 | Davison | A61C 13/0003 700/98 |
| 2014/0045167 A1 | 2/2014 | Anderson et al. | |
| 2014/0122382 A1 | 5/2014 | Elster et al. | |
| 2014/0127639 A1* | 5/2014 | Hirabayashi | A61C 19/05 433/24 |
| 2014/0329194 A1* | 11/2014 | Sachdeva | A61C 7/002 433/24 |
| 2014/0343557 A1 | 11/2014 | Mueller | |
| 2015/0272691 A1* | 10/2015 | Kim | A61B 5/0013 345/420 |
| 2015/0297309 A1* | 10/2015 | Bly | G06F 19/3437 700/98 |
| 2015/0328004 A1 | 11/2015 | Mafhouz | |
| 2016/0038243 A1 | 2/2016 | Miller et al. | |
| 2016/0045317 A1* | 2/2016 | Lang | A61F 2/30942 700/98 |
| 2016/0346091 A1 | 12/2016 | Bin Abdul Rahman et al. | |
| 2017/0014169 A1* | 1/2017 | Dean | A61B 34/10 |
| 2017/0108930 A1* | 4/2017 | Banerjee | G06F 3/016 |
| 2017/0273797 A1* | 9/2017 | Gordon | A61F 2/30942 |

OTHER PUBLICATIONS

Cevidanes, Lucia; "3D Surgical Simulation"; 2011; https://www.ncbi.nlm.nih.gov/pmc/articles/PMC2994415/#R8 (Year: 2011).*

Chapuis, Jonas; "A New System for Computer-Aided Preoperative Planning and Intraoperative Navigation During Corrective Jaw Surgery"; 2007; https://ieeexplore.ieee.org/stamp/stamp.jsp?tp=&arnumber=4167891&tag=1 (Year: 2007).*

International Search Reported dated Feb. 27, 2015 from corresponding International Application No. PCT/US2014/067581; 4 pgs.

Gordon et al. "Overcoming Cross-Gender Differences and Challenges in Le Fort-Based, Craniomaxillofacial Transplantation with Enhanced Computer-Assisted Technology." Annals of Plastic Surgery 71.4 (2013): 421-428.

Murphy et al. "Computer-Assisted, Le Fort-Based, Face—Jaw—Teeth Transplantation: A Pilot Study on System Feasibility and Translational Assessment." International journal of computer assisted radiology and surgery, 2014.

Bell, R. Bryan; "Computer Planning and Intraoperative Navigation in Orthognathic Surgery"; Journal of Oral and Maxillofacial Surgery; 2011, vol. 69, No. 3, pp. 592-605.

Chapuis et al., "A new approach for 3D computer-assisted orthognathic surgery-first clinical case", Elsevier, International Congress Serier, vol. 1281, May 2005, pp. 1217-1222 (Year: 2005).

Extended European Search Report dated Jul. 27, 2018 in corresponding EP Application No. 15862375, 8 pages.

Extended European Search Report dated May 24, 2018 in corresponding EP Application No. 15862868, 8 pages.

Goh, R. et al., "Customized fabricated implats after previous failed cranioplasty", Journal of Plastic, Reconstructive and Aesthetic Surgery, vol. 63, 2010, pp. 1479-1484.

Internatinal Search Report and Written Opinion in International Application No. PCT/US2015/062521, 12 pages.

International Search Report and Written Opinion dated Mar. 9, 2015 from corresponding International Application No. PCT/US2014/067671; 13 pages.

International Search Report and Written Opinion in International Application No. PCT/US2015/062516,10 pages.

International Search Report and Written Opinion dated Sep. 12, 2016 for PCT/US2016/030447.

International Search Report dated Feb. 24, 2015 from corresponding International Application No. PCT/US2014/067504; 5 pgs.

International Search Report dated Mar. 13, 2015 from corresponding International Application No. PCT/US2014/067167; 5 pgs.

International Search Report dated Mar. 20, 2015 from corresponding International Application No. PCT/US2014/067692; 4 pgs.

International Search Report dated Mar. 5, 2015 from corresponding International Application No. PCT/US2014/067174; 4 pgs.

International Search Report dated Mar. 5, 2015 from corresponding International Application No. PCT/US2014/067656; 5 pgs.

International Search Reported dated Feb. 24, 2015 from corresponding International Application No. PCT/US2014/067504; 11 pgs.

Jalbert et al., "One-step primary reconstruction for complex craniofocial re section with PEEK custom-made Implants", Jounal of Cranio-Maxillo-Facial Surgery, Mar. 2014, vol. 42, No. 2, pp. 141-148.

Lee, M. et al., "Custom implant design for patients with craniel defects", Engineering in Medicine and Biology Magazine, IEEE, 2002, vol. 21, pp. 38-44.

Murphy et al., "Computer-assisted single-stage cranioplasty", IN: Engineering in Medicine and Biology Sociaty (EMBC), Aug. 25-29, 2015, pp. 4910-4912.

Schramm et al.; "Non-invasive Registration in Computer Assisted Craniomaxillofacial Surge"; Rechner-und Sensorgestutzte Chirurgie, 2001, pp. 258-268.

Examination Report in Australian Corresponding Application No. 2015353601 dated Jul. 29, 2019, 4 pages.

Non Final Office Action in U.S. Appl. No. 15/100,252 dated Sep. 25, 2019, 9 pages.

Notice of Allowance in U.S. Appl. No. 15/100,258 dated Sep. 11, 2019, 6 pages.

Final Office Action in U.S. Appl. No. 15/529,042 dated Sep. 4, 2019, 9 pages.

Final Office Action in U.S. Appl. No. 15/100,229 dated Oct. 21, 2019, 48 pages.

* cited by examiner

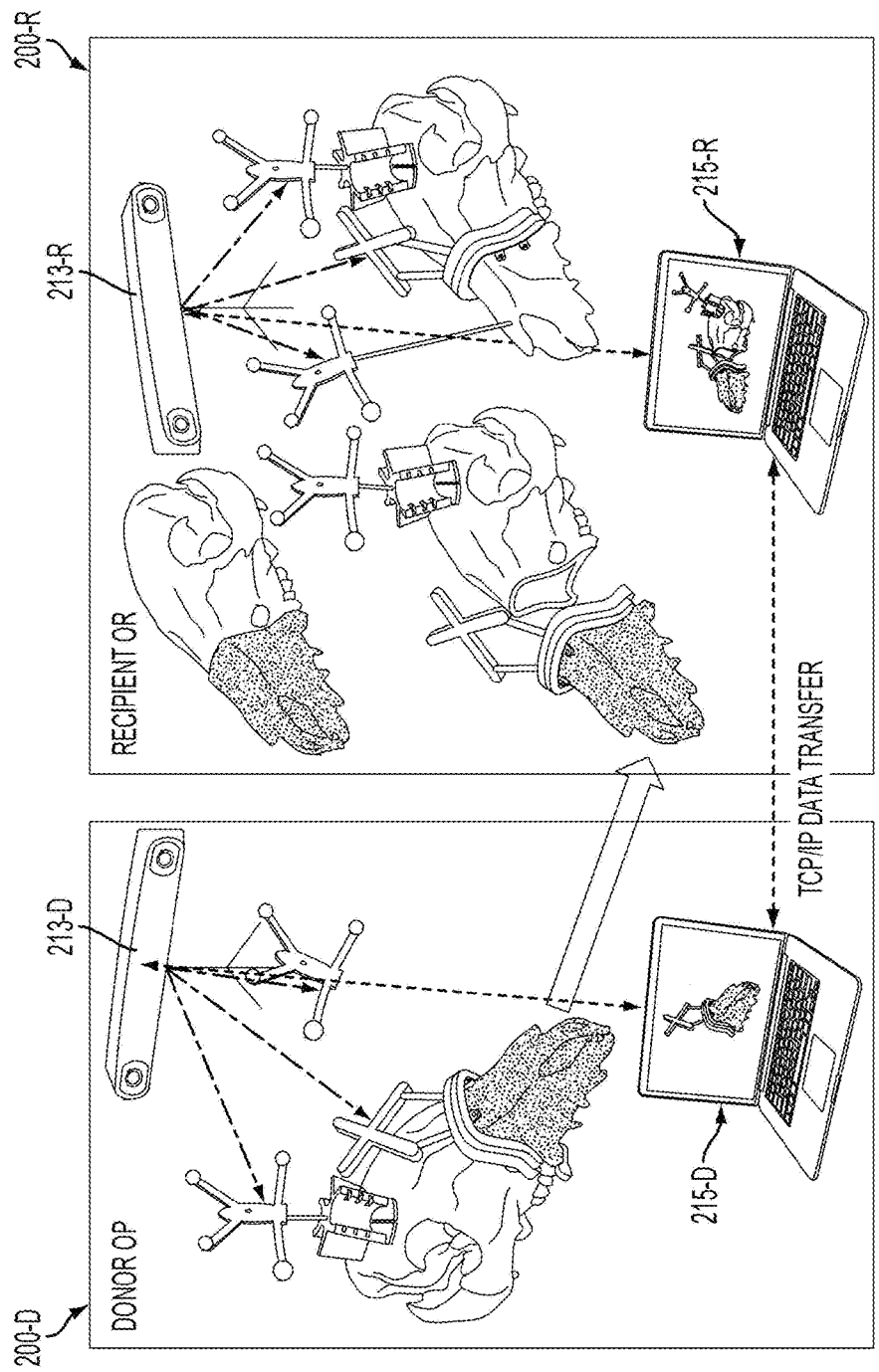
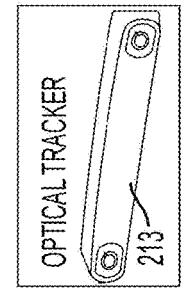
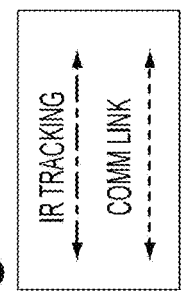
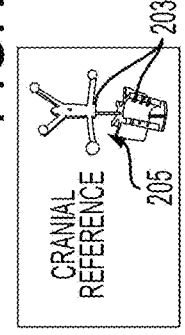
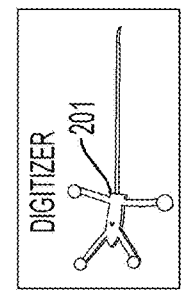

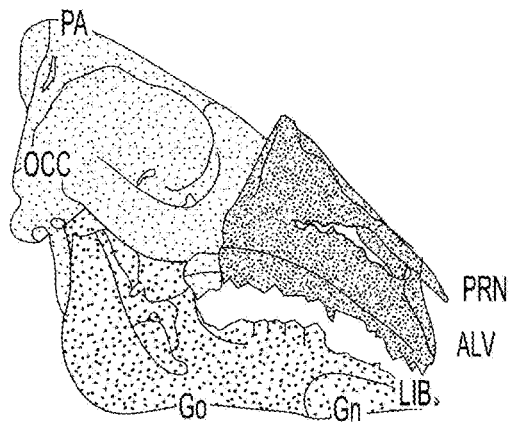
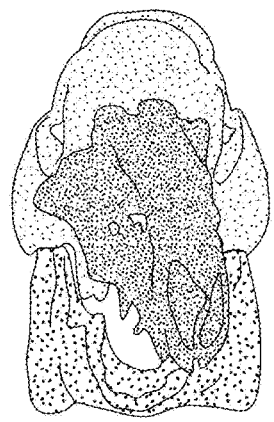
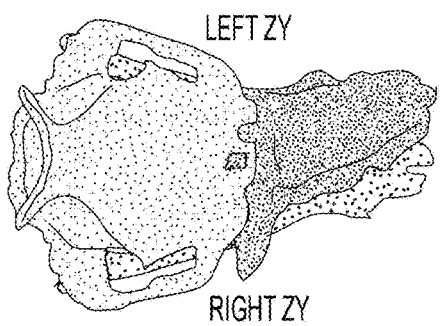
| | |
|---|---|
| LIB-PA-ALV | 8° |
| PA-PRN-ALV | 105° |
| PA-PRN-LIB | 89° |
| ALV-PRN-LIB | 16° |
| OCC-PRN | 184 |
| ZY-ZY | 84 |
| PA-PRN | 191 |
| Go-Gn | 62 |
| Go-LIB | 90 |
| PA-ALV | 197 |
| LIB-ALV | 35 |
| Overbite | -10 |
| Overjet | -7 |
FIG. 5A

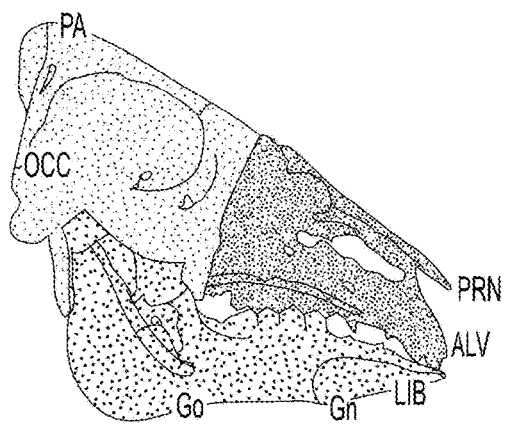
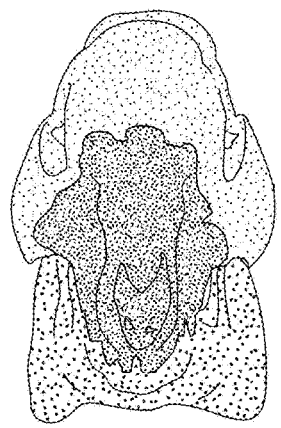
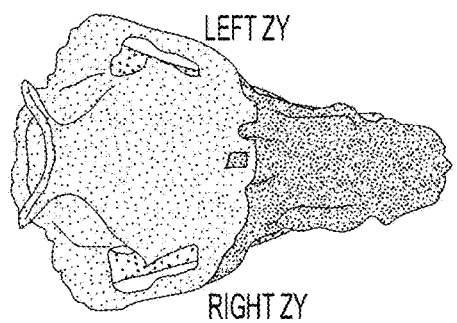
| | |
|---|---|
| LIB-PA-ALV | 7° |
| PA-PRN-ALV | 112° |
| PA-PRN-LIB | 84° |
| ALV-PRN-LIB | 28° |
| OCC-PRN | 186 |
| ZY-ZY | 84 |
| PA-PRN | 191 |
| Go-Gn | 62 |
| Go-LIB | 90 |
| PA-ALV | 200 |
| LIB-ALV | 27 |
| Overbite | -2 |
| Overjet | -3 |
FIG. 5B

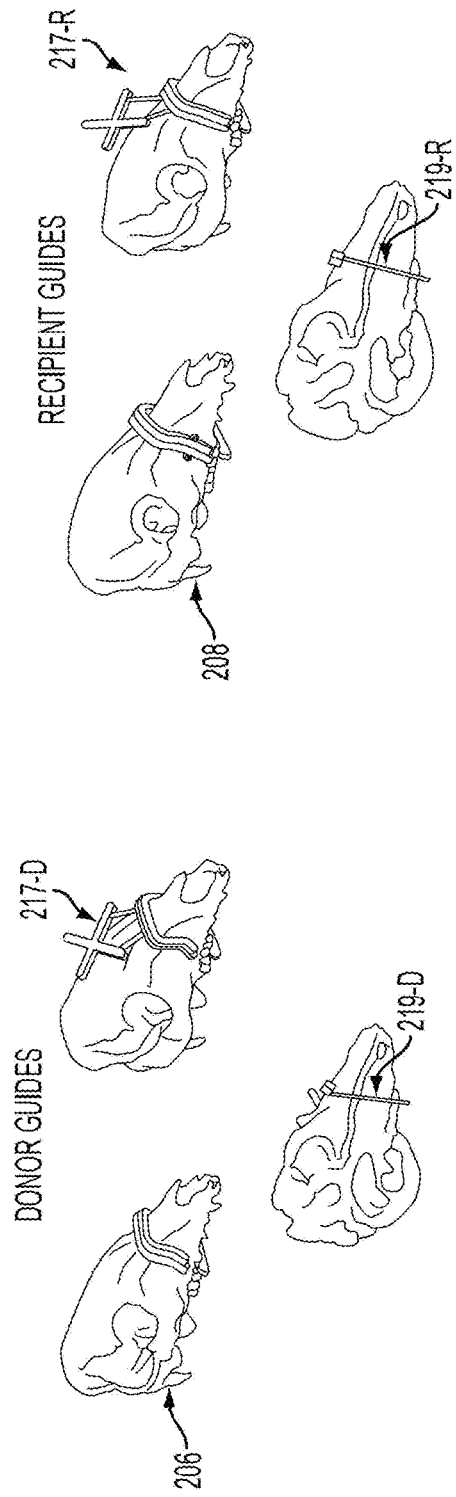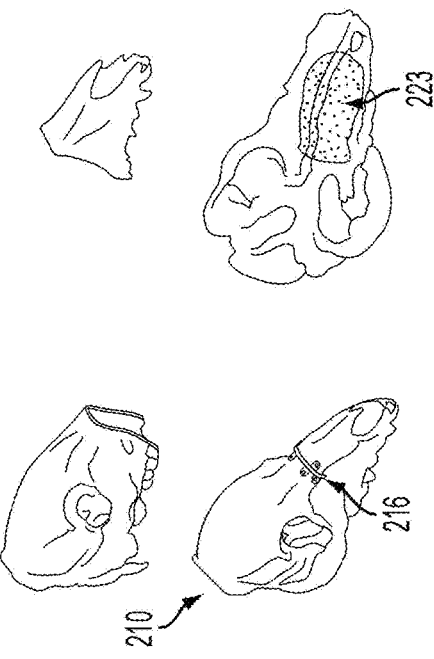
FIG. 8A  DONOR GUIDES
FIG. 8B  RECIPIENT GUIDES
FIG. 8C  "HYBRID" RECIPIENT PALATAL SPLINT AND CUSTOM FIXATION PLATE

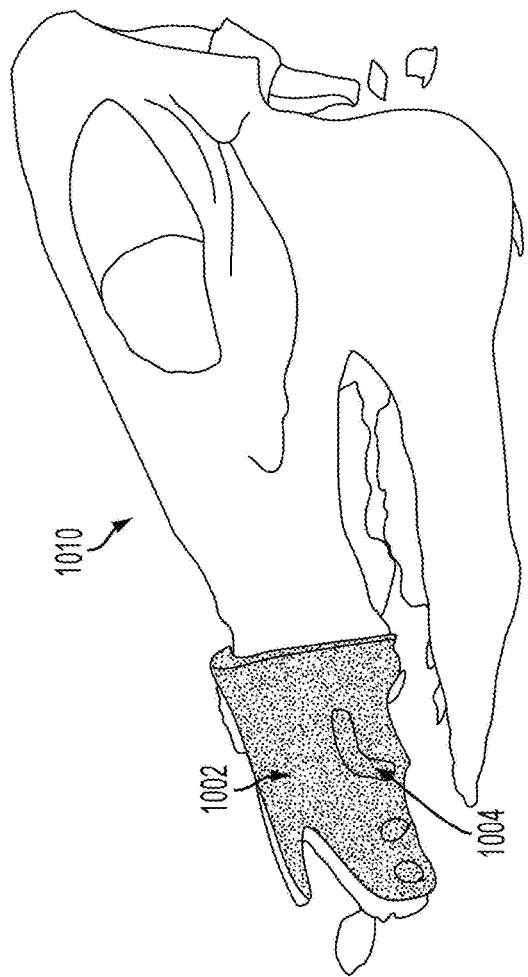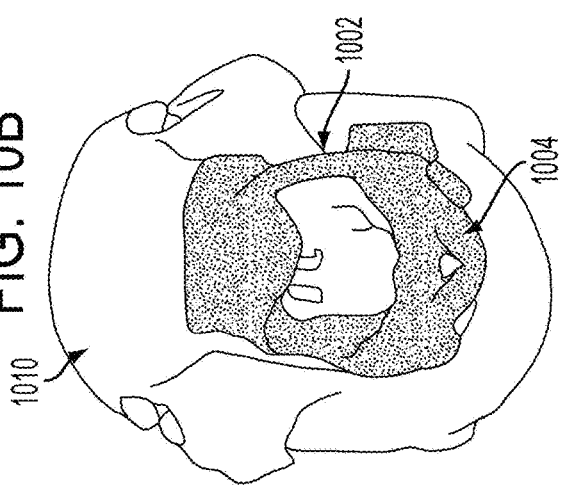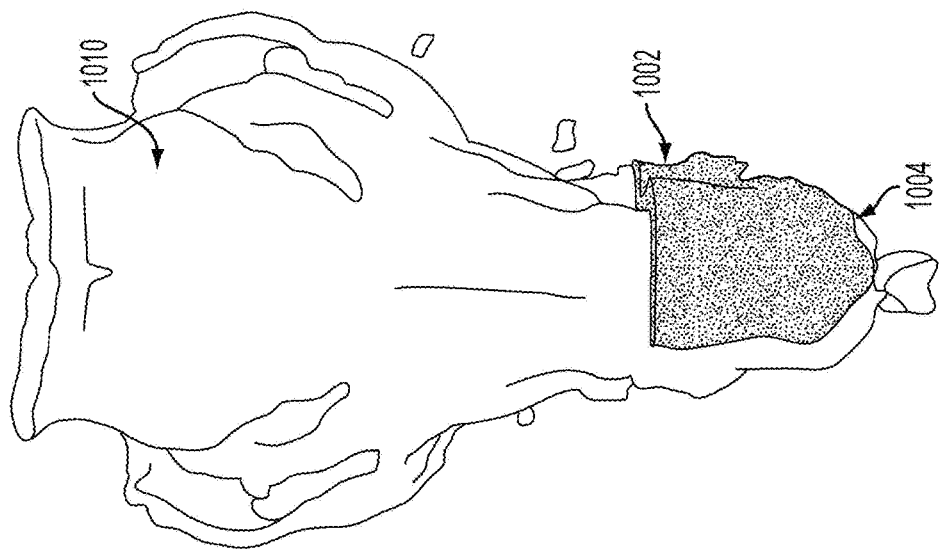

ORTHOGNATHIC BIOMECHANICAL SIMULATION

CROSS-REFERENCE TO RELATED APPLICATIONS

This application is a U.S. National Stage application of PCT/US2014/067581 filed 26 Nov. 2014, which claims priority to U.S. Provisional patent application 61/910,204 filed 29 Nov. 2013, U.S. provisional application 61/940,196 filed 14 Feb. 2014, and U.S. provisional application 62/049,866 filed 12 Sep. 2014, the entire disclosures of which are hereby incorporated by reference in their entireties.

GOVERNMENT SUPPORT STATEMENT

This invention was made with government support under NCATS Grant No. UL1TR000424-06 awarded by the National Institutes of Health. The government has certain rights in the invention.

FIELD OF THE INVENTION

This invention relates generally to the field of surgery, particularly craniomaxillofacial surgery, and specifically to the field of computer-assisted craniomaxillofacial surgery and all related orthognathic, neurosurgical and head/face/neck surgical procedures and associated methods, tools, and systems.

BACKGROUND OF THE INVENTION

Facial transplantation represents one of the most complicated scenarios in craniomaxillofacial surgery due to skeletal, aesthetic, and dental discrepancies between donor and recipient. Use of computer technology to improve accuracy and precision of craniomaxillofacial surgical procedures has been described for nearly 30 years, since the increasing availability of computed topography (CT) prompted the development of a CT-based surgical simulation plan for osteotomies.

Two broad approaches to computer-assisted surgery (CAS) have gained popularity: 1) pre-operative computer surgical planning and the use of three-dimensional computer manufactured surgical guides (3D CAD/CAM) to cut and reposition bone and soft tissue, and 2) utilizing intraoperative feedback relative to preoperative imaging for the surgeon to provide more objective data on what is happening beyond the "eyeball test." However, none are meant for real-time placement feedback in areas where guide placement is more challenging, such as the three-dimensional facial skeleton. Also, there are no single platforms built to provide BOTH planning AND navigation—with seamless integration. Additionally, standard off-the-shelf vendor computer-assisted surgery systems may not provide custom features to mitigate problems associated with the increased complexity of this particular procedure. Furthermore, there are currently no validated methods for optimizing outcomes related to facial (e.g., soft tissue), skeletal (e.g., hard tissue), and occlusal (e.g., dental) inconsistencies and for predicting post-operative function (e.g., mastication) in the setting of a donor-to-recipient anthropometric mismatch—a major hurdle to achieving this specialty's full potential.

One known system includes pre-operative planning and cutting guides by way of computer manufactured stereolithographic models for human facial transplantation. However, such a system uses standard off-the-shelf vendor systems and does not include necessary features to mitigate the increased complexity of this particular procedure.

Additionally, known CAS paradigms for craniomaxillofacial surgery provide little capacity for intraoperative plan updates. This feature becomes especially important since, in some circumstances during the transplantation surgery, it may be necessary to revise and update the preoperative plans intraoperatively.

What is needed in the art, therefore, is a single, fully-integrated platform, providing a computer-assisted surgery solution customized for pre-operative planning, intraoperative navigation, and dynamic, instantaneous feedback, for example, in the form of biomechanical simulation and real-time cephalometrics, for post-operative function prediction in facial transplantation that addresses common shortcomings of existing CAS systems and has the potential to improve outcomes across both the pediatric and adult-based patient population.

SUMMARY

According to some embodiments, a method of simulating mastication is disclosed. The method includes obtaining a computer-readable three-dimensional representation of a first skeletal fragment comprising a portion of at least one of a mandible and a maxilla, obtaining a computer readable three-dimensional representation of a recipient skeletal fragment comprising a portion of at least one of a mandible and a maxilla, obtaining placement data representing a position of at least a portion of the first skeletal fragment relative to at least a portion of the recipient skeletal fragment, obtaining muscle insertion data representing at least one muscle insertion location on at least one of the first skeletal fragment and the recipient skeletal fragment, simulating a contraction of a muscle positioned according to the muscle insertion data in a representation of a surgical hybrid comprising at least a portion of the first skeletal fragment positioned according to the placement data relative to at least a portion of the recipient skeletal fragment, and outputting a representation of mastication represented by the simulating.

Various optional features of the above embodiments include the following. The obtaining placement data may include obtaining placement data prior to a surgery to transplant at least a portion of the first skeletal fragment into a recipient. The obtaining placement data may include obtaining placement data during a surgery to transplant at least a portion of the first skeletal fragment into a recipient. The obtaining placement data may include tracking a position of at least a portion of the first skeletal fragment during the surgery. The method may include obtaining muscle activation data representing at least one muscle contraction, where the simulating includes simulating a contraction of a muscle according to the muscle activation data.

According to some embodiments, a method of simulating mastication is disclosed. The method includes obtaining a computer-readable three-dimensional representation of an osseointegrative implant comprising a portion of at least one of a mandible and a maxilla, obtaining a computer readable three-dimensional representation of a recipient skeletal fragment comprising a portion of at least one of a mandible and a maxilla, obtaining placement data representing a position of at least a portion of the osseointegrative implant relative to at least a portion of the recipient skeletal fragment, obtaining muscle insertion data representing at least one muscle insertion location on at least one of the osseointegrative implant and the recipient skeletal fragment, simulating a contraction of a muscle positioned according to the muscle insertion data in a representation of a surgical hybrid comprising at least a portion of the osseointegrative implant positioned according to the placement data relative to at least a portion of the recipient skeletal fragment, and outputting a representation of mastication represented by the simulating.

Various optional features of the above embodiments include the following. The obtaining placement data may include obtaining placement data prior to a surgery to implant at least a portion of the osseointegrative implant into a recipient. The obtaining placement data may include obtaining placement data during a surgery to implant at least a portion of the osseointegrative implant into a recipient. The obtaining placement data may include tracking a position of at least a portion of the osseointegrative implant during the surgery. The method may also include obtaining muscle activation data representing at least one muscle contraction, wherein the simulating includes simulating a contraction of a muscle according to the muscle activation data.

According to some embodiments, a system for simulating mastication is disclosed. The system includes at least one electronic memory and at least one electronic processor, the at least one electronic memory including instructions which, when executed by the at least one electronic processor, cause the at least one electronic processor to perform a method including: obtaining a computer-readable three-dimensional representation of a first skeletal fragment comprising a portion of at least one of a mandible and a maxilla, obtaining a computer readable three-dimensional representation of a recipient skeletal fragment comprising a portion of at least one of a mandible and a maxilla, obtaining placement data representing a position of at least a portion of the first skeletal fragment relative to at least a portion of the recipient skeletal fragment, obtaining muscle insertion data representing at least one muscle insertion location on at least one of the first skeletal fragment and the recipient skeletal fragment, simulating a contraction of a muscle positioned according to the muscle insertion data in a representation of a surgical hybrid comprising at least a portion of the first skeletal fragment positioned according to the placement data relative to at least a portion of the recipient skeletal fragment, and outputting a representation of mastication represented by the simulating.

Various optional features of the above embodiments include the following. The obtaining placement data may include obtaining placement data prior to a surgery to transplant at least a portion of the first skeletal fragment into a recipient. the obtaining placement data may include obtaining placement data during a surgery to transplant at least a portion of the first skeletal fragment into a recipient. The obtaining placement data may include tracking a position of at least a portion of the first skeletal fragment during the surgery. The at least one electronic memory may further include instructions which, when executed by the at least one electronic processor, further cause the at least one electronic processor to obtain muscle activation data representing at least one muscle contraction, where the simulating includes simulating a contraction of a muscle according to the muscle activation data.

According to some embodiments, a system for simulating mastication is disclosed. The system includes at least one electronic memory and at least one electronic processor, the at least one electronic memory including instructions which, when executed by the at least one electronic processor, cause the at least one electronic processor to perform a method including: obtaining a computer-readable three-dimensional representation of an osseointegrative implant comprising a portion of at least one of a mandible and a maxilla, obtaining a computer readable three-dimensional representation of a recipient skeletal fragment comprising a portion of at least one of a mandible and a maxilla, obtaining placement data representing a position of at least a portion of the osseointegrative implant relative to at least a portion of the recipient skeletal fragment, obtaining muscle insertion data representing at least one muscle insertion location on at least one of the osseointegrative implant and the recipient skeletal fragment, simulating a contraction of a muscle positioned according to the muscle insertion data in a representation of a surgical hybrid comprising at least a portion of the osseointegrative implant positioned according to the placement data relative to at least a portion of the recipient skeletal fragment, and outputting a representation of mastication represented by the simulating.

Various optional features of the above embodiments include the following. The obtaining placement data may include obtaining placement data prior to a surgery to implant at least a portion of the osseointegrative implant into a recipient. The obtaining placement data may include obtaining placement data during a surgery to implant at least a portion of the osseointegrative implant into a recipient. The obtaining placement data may include tracking a position of at least a portion of the osseointegrative implant during the surgery. The at least one electronic memory may further include instructions which, when executed by the at least one electronic processor, further cause the at least one electronic processor to obtain muscle activation data representing at least one muscle contraction, wherein the simulating includes simulating a contraction of a muscle according to the muscle activation data.

Additional advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIGS. 2A-2C provide a schematic overview of a surgical system.

FIGS. 2D-2G are graphical representations of some components and/or features of the surgical system of FIGS. 2A-2C.

FIGS. 5A-5B show depictions of on-screen images provided by a surgical system, such as the surgical system of FIG. 2A displaying real-time, dynamic cephalometrics and pertinent measurements applicable to humans. FIG. 5A shows a donor's face-jaw-teeth alloflap in suboptimal position as compared to a recipient's cranium. FIG. 5B shows appropriate face-jaw-teeth positioning with immediate surgeon feedback and updated cephalometric data pertinent to a pre-clinical investigation. A surgeon may adjust the position of face-jaw-teeth segment upwards, downwards, forwards, or backwards based on this real-time cephalometric feedback, as this information helps to predict optimal form and function. For instance, placing the face-jaw-teeth segment forward may improve the patient's airway, but if moved too far forward, it may cause the patient to have a significant overjet (i.e. malocclusion) and abnormal appearance in a profile view.

FIGS. 8A-8C are illustrations of cutting guides of the embodiments with navigational capabilities. FIG. 8A illustrates a donor face-jaw-teeth alloflap recovery, FIG. 8B shows a recipient preparation prior to transplant, and FIG. 8C illustrates a custom pre-bent fixation plate and palatal splint designed to achieve face-jaw-teeth alignment and skeletal inset.

FIGS. 10A-10C are a top-view (bird's eye view), a left-sided profile view, and a frontal view, respectively, of images displayed by an imaging system of a surgical system. The images depict a recipient skeleton and include real-time assessment of planned versus actual face-jaw-teeth positions.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Disclosed are embodiments of a computer-assisted surgery system that provides for large animal and human pre-operative planning, intraoperative navigation which includes trackable surgical cutting guides, and dynamic, real-time instantaneous feedback of biomechanical simulation and cephalometric measurements/angles as needed for medical procedures, such as facial transplantation, and many other instances of craniomaxillofacial and orthognathic surgery. Such a system can be referred to as a computer-assisted planning and execution (C.A.P.E.) system and can be exploited in complex craniomaxillofacial surgery like Le Fort-based, face-jaw-teeth transplantation, for example, and any type of orthognathic surgical procedure affecting one's dental alignment, and can include cross-gender facial transplantation.

Figure 1:
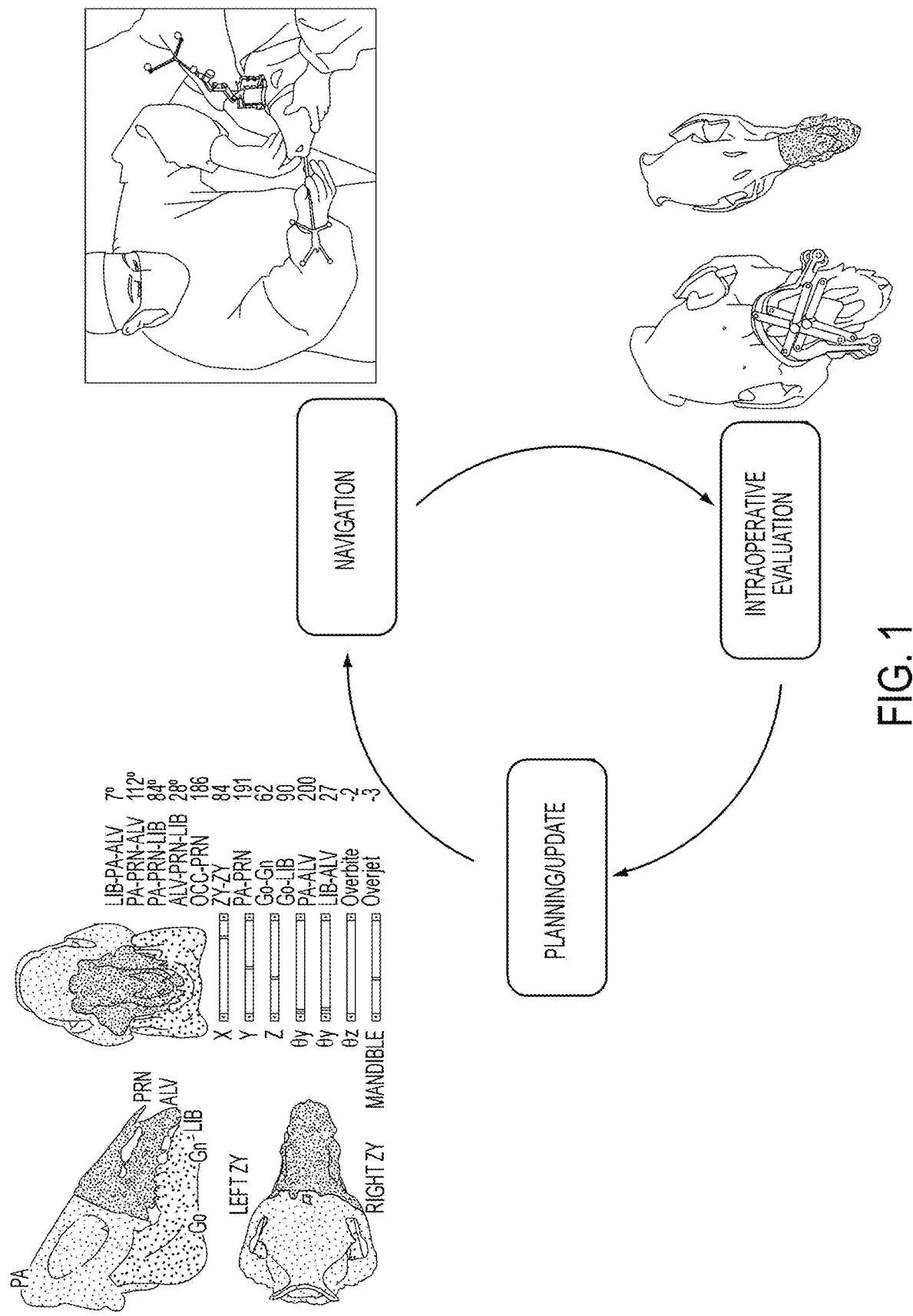
FIG. 1 is a flowchart of a surgical system and method that closes the loop between surgical planning, navigation, and enabling intraoperative updates to a surgical plan.
Figure 2A:
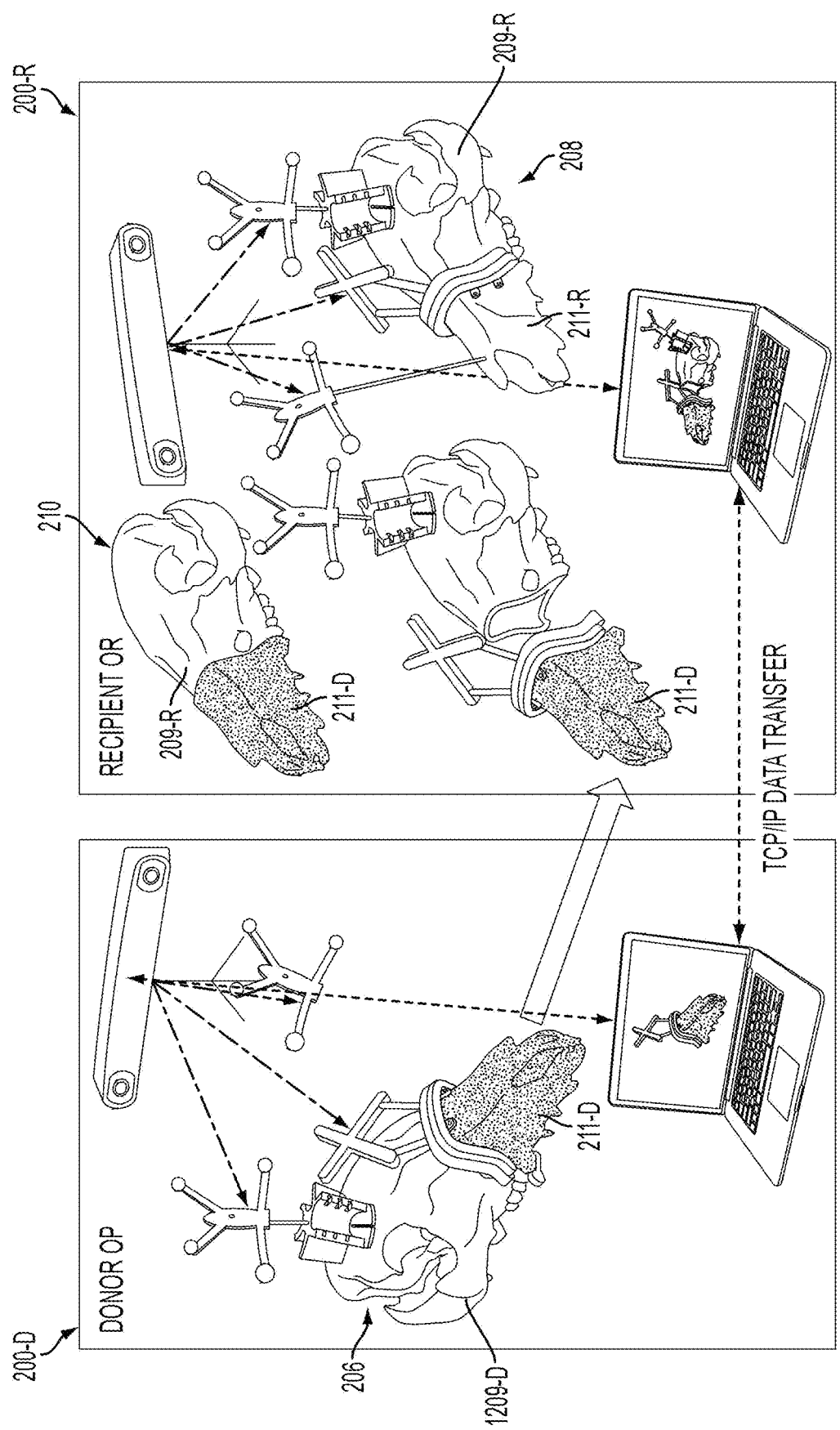
Figure 2B:
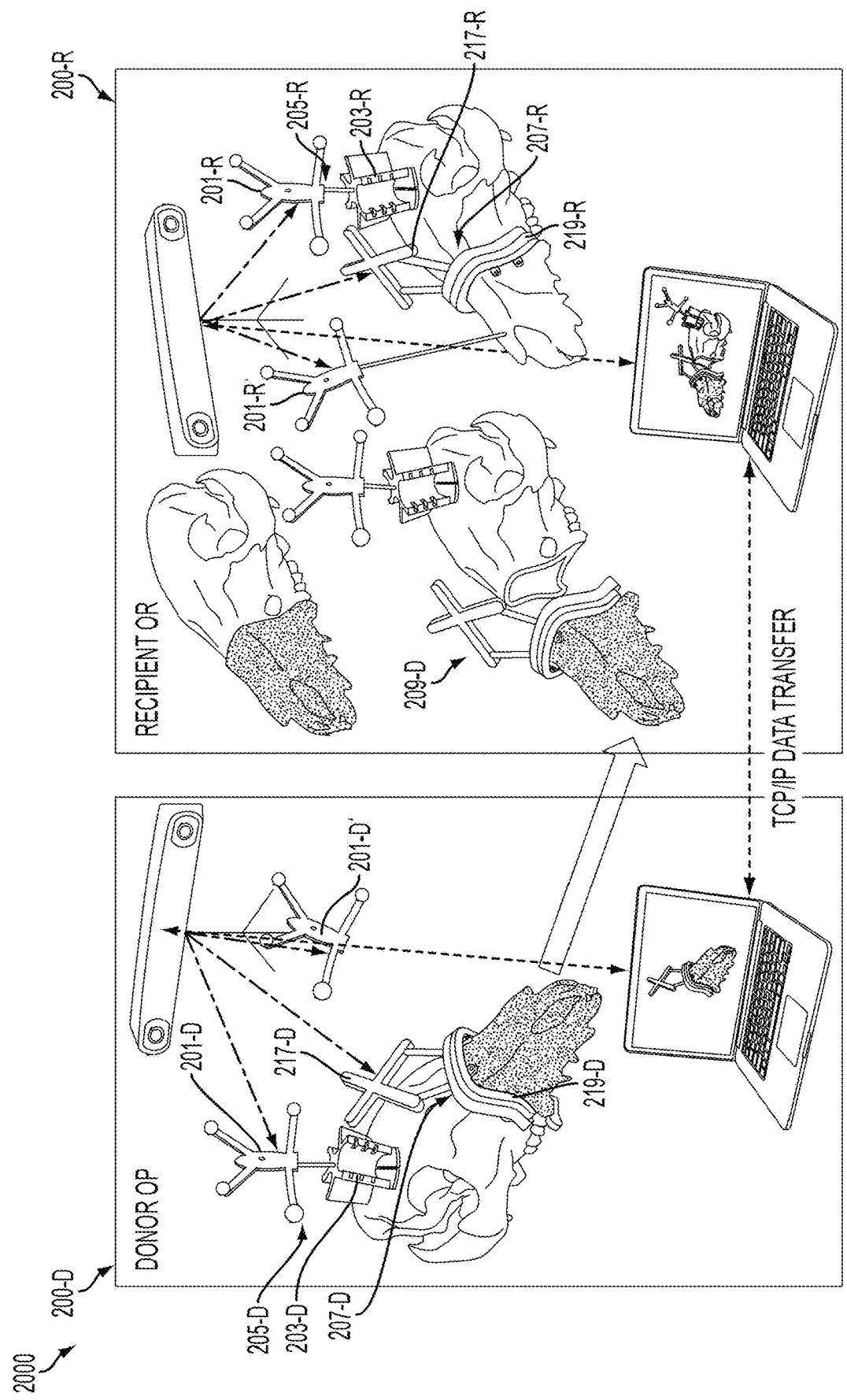

The fundamental paradigm for computer-assisted surgery (CAS) involves developing a surgical plan, registering the plan and instruments with respect to the patient, and carrying out the procedure according to the plan. Embodiments described herein include features for workstation modules within a CAS paradigm. As shown in FIG. 1, a surgical system of the embodiments can enable intraoperative evaluation of a surgical plan and can provide instrumentation for intraoperative plan updates/revisions when needed.

Embodiments can include a system with integrated planning and navigation modules, for example, a system for tracking donor and recipient surgical procedures simultaneously. In general, features of such a system can include: 1) two or more networked workstations concurrently used in planning and navigation of the two simultaneous surgeries for both donor and recipient irrespective of geographic proximity, 2) two or more trackers, such as electromagnetic trackers, optical trackers (e.g., Polaris, NDI Inc.), and the like, for tracking bone fragments, tools, and soft tissues, 3) one or more guides, reference kinematic markers, etc. as required for navigation. These features are described in further detail with respect to FIGS. 2A-2G.

Preoperative planning can include the following tasks: a) segmentation and volumetric reconstruction of the donor and recipient facial anatomy; b) planning for patient-specific cutting guide placement; c) cephalometric analysis and biomechanical simulation of the hybrid skeleton's occlusion and masticatory function, respectively; d) fabrication of the hybrid cutting guides enabling both geometric ("snap-on" fit) and optical navigation; e) 3D mapping the vascular system on both recipient and donor facial anatomy; and f) plan updates, if necessary, based on the feedback from the intraoperative module. As used herein, "snap-on fit" or "snap-on" or "snap on" are used to describe the way an item, such as a cutting guide, attaches to a pre-determined area. That is, the cutting guide actually "snaps-on" to a certain pre-determined area along the patient being's anatomy, such as the facial skeleton, and in all other areas it doesn't fit properly since size and width varies throughout significantly with many convexities and concavities.

Intraoperative tasks of embodiments described herein can generally include: 1) registering the preoperative model reconstructed from the CT data to donor and recipient anatomy; 2) visualizing (e.g., using information from the tracker, such as an electromagnetic tracker, optical tracker, and the like) the instruments and cutting guides to help the surgeon navigate; 3) verifying the placement of cutting guides, and performing real-time cephalometric and biomechanical simulation for occlusion analysis, if, for any reason, the osteotomy sites need to be revised; 4) dynamically tracking the attachment of the donor fragment to the recipient and providing quantitative and qualitative (e.g., visual) feedback to the surgeon for the purpose of improving final outcomes related to form (i.e., overall facial aesthetics) and function (i.e., mastication, occlusion relation, airway patency). Such a procedure is described in further detail below with respect to FIG. 3.

Preoperative Planning

In general, a method for performing a surgery includes a virtual surgical planning step that includes performing segmentation and 3D reconstruction of recipient and donor CT scans (e.g., Mimics 15.01, Materialise, Leuven Belgium). Virtual osteotomies can then be performed within the software to optimize the donor/recipient match. Patient-customized cutting guide templates can then be created (3-matic 7.01, Materialize, Leuven, Belgium). These templates can then be rapid-prototyped via an additive manufacturing modeling process, which can include, but is not limited to, stereolithography or 3D printing and the like. The surgical method and system for performing surgery are described in further detail below.

Figure 4B:
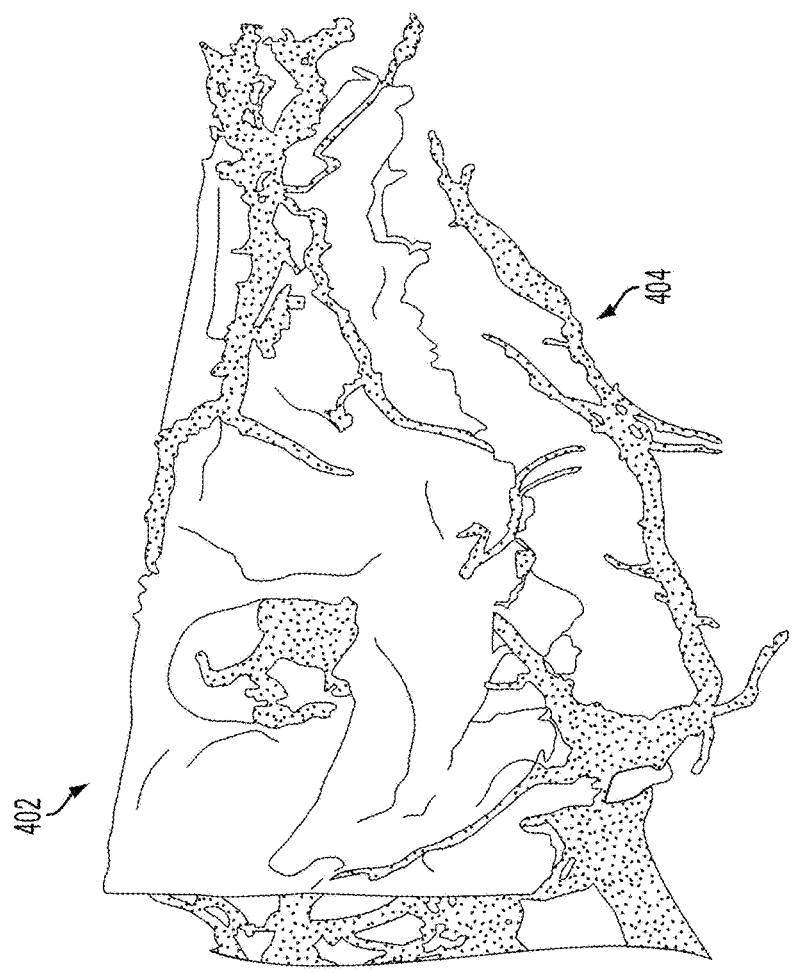
FIG. 4B shows a segmented arterial system of a craniomaxillofacial skeleton generated from CT angiography (CTA) data allowing 3D, intraoperative mapping.
Figure 4A:
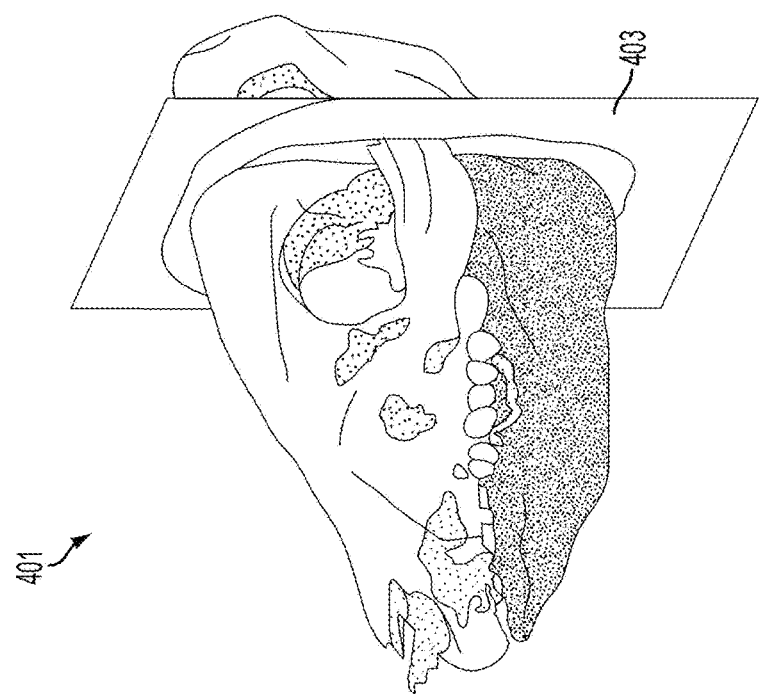
FIG. 4A is a CT-scan of reconstructed images of a size-mismatched facial skeleton generated from segmentation software utilized for pre-operative planning.

Referring to FIGS. 4A and 4B, during the initial planning stage, surgeons determine a virtual plan 401 based on the recipient's craniomaxillofacial deformity irrespective of the donor. From registered CT data, segmentation software generates volume data for specific key elements (e.g., the mandible, maxilla, and cranium) used for preoperative planning and visualization. The planning workstation automatically generates the expected cut geometry of the donor fragment 402 together with the recipient, thereby defining the predicted facial skeleton with accompanying hybrid occlusion. If available, blood vessels 404 are segmented from CT angiography scans as shown in FIG. 4B. That is, in an embodiment, nerves (via known nerve foramens) and vessels (both arteries and veins) can be localized to provide a full anatomical "road map" to the surgeons for a more precise, time-saving anatomical dissection with perhaps decreased blood loss and smaller incisions. The planning module can also perform predictive biomechanical simulation and cephalometric analysis related to face-jaw-teeth harmony on varying constructions of the hybrid donor and recipient jaw, such as that shown in FIGS. 5A-5B. Using this tool, the surgeon can evaluate different placements for the donor's face-jaw-teeth alloflap on the recipient's facial skeleton in relation to orbital volumes, airway patency, facial projection, and dental alignment. An automated cephalometric computation for the hybrid face indicates the validity of the planned surgery from both an aesthetic, functional and reconstructive standpoint based on various measurements of pertinent landmarks as shown, for example, in Tables 1A-B.

TABLE 1A

Pertinent landmarks for cephalometric analysis

| SYMBOL | NAME and DEFINITION |
|---|---|
| Go | Gonion: a point mid-way between points defining angles of the mandible |
| Gn | Gnathion: most convex point located at the symphysis of the mandible |
| ALV | Alveolare: mid-line of alveolar process of the upper jaw, at incisor - alveolar junction |
| LIB | Lower Incisor Base: midline of anterior border of alveolar process of mandible at the incisor-alveolar junction |
| PA | Parietale: most superior aspect of skull in the midline, (formed by nuchal crest of occipital bone and parietal bone) |
| PRN | Pronasale: bony landmark representing anterior limit of nasal bone |
| ZY | Zygion: most lateral point of malar bone |
| OCC | Occipital region: midpoint between the occipital condyles |

TABLE 1B

Cephalometric measurements and related units.

| | Measure | | | | | | | | | | | |
|---|---|---|---|---|---|---|---|---|---|---|---|---|
| | ZY-ZY | PA-PRN | Go-Gn | Go-LIB | PA-ALV | LIB-ALV | Overbite | Overjet | OCC-PRN | LIB-PA-ALV | PA-PRN-ALV | PA-PRN-LIB | ALV-PRN-LIB |
| Units | mm | mm | mm | Mm | mm | mm | Mm | mm | mm | deg | deg | deg | deg |

To evaluate and predict cephalometric relationships both during planning and intra-operative environments, the system can use validated, translational landmarks between swine and human to thereby allow effective pre-clinical investigation. The cephalometric parameters defined by these landmarks can be automatically recalculated as the surgeon relocates the bone fragments using a workstation's graphical user interface.

Figure 6:
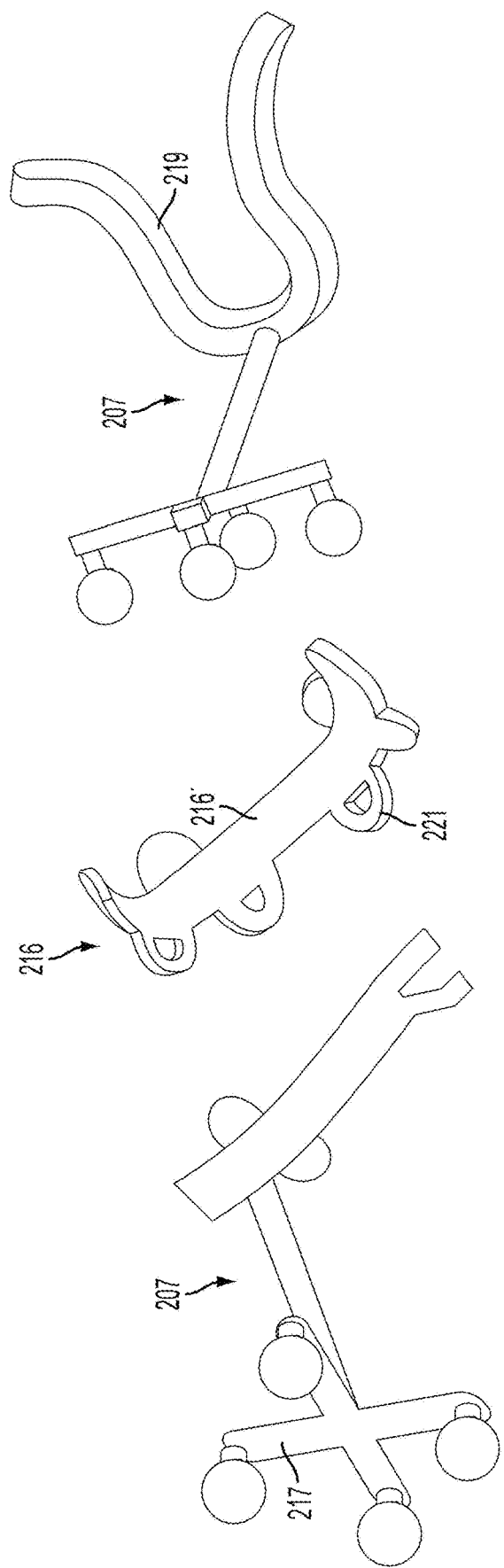
FIG. 6 shows some pre-bent fixation plates with screw holes designed virtually to accommodate the donor-to-recipient skeletal mismatch areas and matching navigational cutting guides of a surgical system, for example, the surgical system of FIGS. 2A-2C.

Preoperative planning can also involve fabrication of custom guides 207 (as shown in FIG. 6) and palatal splints 223 (as shown in FIG. 8C). Planned cut planes 403 (as shown in FIG. 4) can be used for defining the geometry of the cutting guides to thereby provide patient-specific cutting guides. These cutting guides can be designed according to the skeletal features through which the cutting plane intersects, such as an outer skeletal surface of a cross section defined by the cutting plane, and can be fabricated via stereolithography, or via any additive manufacture technology. In an embodiment, custom guide t m plates can be separately designed and navigational registration elements can be added (Freeform Plus. 3D Systems, Rock Hill, S.C.). As discussed above, the surgical guides can be manufactured via additive manufacturing technology (AMT). The cutting guides can, therefore, be a 3D printing material such as a polymer, and can include an attachment surface 216 configured for attaching to a skeletal feature, and can have a "snap-on" fit to both donor and recipient. As described above, the attachment surface may include a contoured surface that corresponds to the contours of the skeletal feature within the planned cut planes. A navigation surface, such as a reference geometry 217 connected, built into, or attached to the guide structure directly or via attachment guides (not shown), enables dynamic intraoperative tracking of guides with respect to the patient's skeleton. Palatal splints ensure planned dento-skeletal alignment fixation following Le Fort-type facial transplants or any similar type of surgery. Fixation plates 216 can include a primary surface 216' and a plurality of fixation surfaces 221, such as eyelets, for screw placement to provide rigid immobilization at the irregular skeletal contour areas along various donor-to-recipient interfaces. Having pre-bent fixation plates decreases total operative times and helps to confirm accurate skeletal alignment by overcoming step-off deformities at bone-to-bone interfaces. Accordingly, at least one of the plurality of fixation surfaces can be located on one side of the primary surface and configured for attaching the fixation surface to a donor skeleton fragment, and at least one of another of the plurality of fixation surfaces is located on another side of the primary surface and configured for attaching the fixation surface to a recipient skeleton. The whole fixation plate or just portions of the fixation plate, such as the primary surface or fixation surfaces can be manufactured via additive manufacturing technology.

The cutting guide's navigation surface can include trackable objects, for example, on the reference geometry, such as infrared (IR) reflective coatings or IR emitters. For example, the trackable objects can include a plurality of integrated tracking spheres, each of which has an IR reflection surfaces.

Intraoperative Surgical Assistance

Figure 7B:
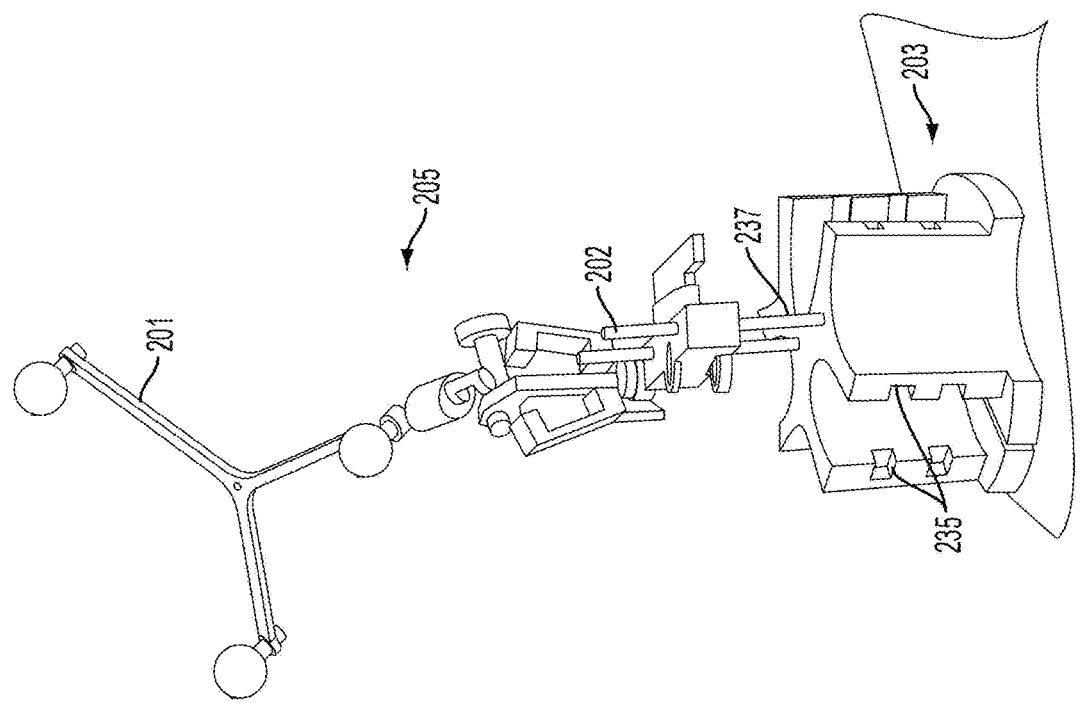
FIG. 7B shows a detachable rigid body with reflective markers attached to the reference body.
Figure 7A:
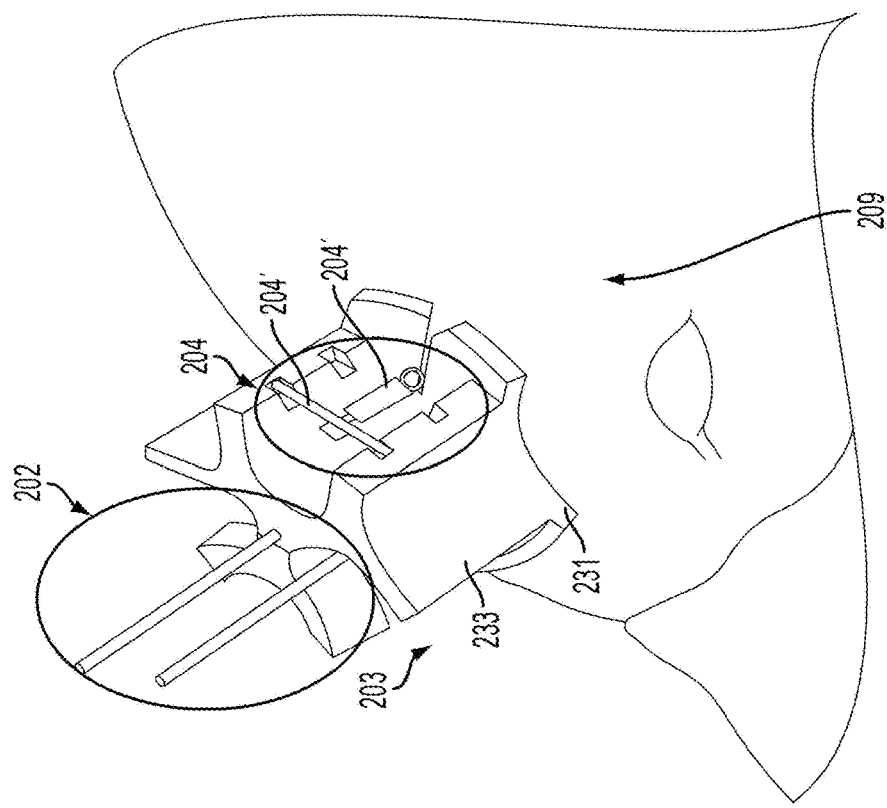
FIG. 7A shows a kinematic reference mount of an embodiment as it is affixed onto a donor's cranium with intermaxillary screws. A permanent suture (not visible) attaches stabilizers, such as springs and/or cross bars, which allow easy removal and replacement during surgery.

Individual navigation for both donor and recipient surgeries tracks the cutting guides with respect to planned positions. Surgeons can attach a reference unit, such as a kinematic reference mount to three intramedullary fixation (IMF) screws arranged in a triangular pattern on each the donor and recipient craniums as shown in FIG. 7A-7B. Accordingly, in an embodiment, there is a reference unit 205 for providing real-time surgical navigation assistance. The reference unit for providing real-time surgical navigation assistance can include a kinematic mount 203, at least one fixation rod 202, at least one support 204, and reference geometry 201. The kinematic mount 203 can include a base with a plurality of recesses defined by sidewalls 233, at least one pair of slots 235 defined by portions of the sidewalls, with each slot of the pair formed across the recess from the other slot, and at least one guide hole 237 extending through a length of the fixation plate. The at least one fixation rod 202 can extend through the at least one guide hole 237. An end of the at least one support rod can be configured for attaching to a skeleton of a being 209. The at least one support can be disposed in the pair of slots and can be configured to attach to the being. The reference geometry 201 can be attached to the at least one fixation rod.

The at least one support 204 can include at least one cross-bar 204' with ends that are configured for placement in the slots 235, and a spring 204" attached at one end to the at least one cross-bar 204' and attached at another end to the patient (e.g., a human-being). The spring attached at another end to the being can be attached via a suture (further described below). The reference unit 205 can further include a trackable object disposed on the reference geometry. The trackable object disposed on the reference geometry can include an IR reflective surface. The mount 203 can be made via additive manufacturing techniques and can therefore include a polymer. The at least one fixation rod can include a plurality of intramedullary fixation screws. The base can be configured for being detachably mounted on the skeleton of the being 209. The intramedullary fixation screws can be arranged in a triangular pattern. Accordingly the guide-holes can be configured in a triangular pattern on the base.

Accordingly, the mount design permits flexibility in the placement of the IMF screws so that no template is necessary. A spring 204" can attach to each IMF screw via suture threaded through, for example, the eyelets. These springs hold the cranial mount 203 in place and allow easy removal and replacement of the cranial mount (e.g. during positional changes required for bone cuts and soft tissue dissections). This may provide detachability and use of Intramaxillary fixation (IMF) screws for stable attachment The reference geometry 201 (e.g., which can be purchased from Brainlab, Westchester, Ill., USA) attached to the kinematic mount 203 provides a static coordinate frame attached to the patient. The surgeon can digitize three bony landmarks (e.g., the inferior aspect of the orbits and antero-superior maxilla) to define a rough registration between the environment and virtual models. For example, three, consistent points can be selected which can be quick to find, easy to reproduce on numerous occasions, and would remain constant irrespective of the user and his/her experience with the systems of the embodiments. The surgeon can thereby collect several point sets from exposed bone using a digitization tool and uses an iterative closest point registration technique to refine the registration. As shown in FIG. 8, once registered, the surgeon navigates the placement of the cutting guide 217 using the combination of "snap-on" geometric design and the tracking system coupled to visual feedback. This allows assessment of inaccuracies related to soft tissue interference, iatrogenic malpositioning, and anatomical changes since acquiring original CT scan data, and/or imperfections in cutting guide design or additive manufacturing process.

Self-drilling screws affix the cutting guide to the patient's skeleton to ensure osteotomies are performed along pre-defined planes, maximizing bony congruity. After dissecting the donor's maxillofacial fragment and preparing the recipient's anatomy, the surgical team transfers the facial alloflap. The system is configured to track the final three-dimensional placement of, for example, the Le Fort-based alloflap providing real-time visualization such as that shown in FIG. 5A-5B. This provides real-time visualization of important structures such as new orbital volumes (vertical limit of inset), airway patency (posterior horizontal limit of inset), and facial projection (anterior horizontal limit of inset). Once confirmed, the surgeon fixates the donor alloflap to the recipient following conventional techniques with plates and screws.

Accordingly, returning to FIGS. 2A-2G, there is a system 200 for tracking donor and recipient surgical procedures simultaneously. The system can include a donor sub-system 200-D, a recipient sub-system 200-R and a communications link (indicated by the horizontal dotted-line) such as a communication link that provides TCP/IP data transfer between the donor and recipient sub-systems. The donor sub-system can include a first computer workstation 215-D, a first cranial reference module 205-D, a first cutting guide 207-D for attaching to a preselected location of a donor skeleton 206, a first fragment reference module 201-D', and a first tracker 213-D. The first cutting guide 207-D can include an attachment surface 219-R configured for attaching to a skeletal feature, and a navigation surface 217-D connected to the attachment surface and comprising a trackable reference geometry. The first tracker 213-D may be configured to be in communication with the first computer workstation, for example, via a communications link. The first tracker can be configured to track, for example via IR optical tracking, a location of a portion of the first cranial reference module, a portion of the first cutting guide and a portion of the first fragment reference module. The recipient sub-system 200-R can include a second computer workstation 215-R, a second cranial reference module 205-R, and a second tracker 213-R. The second tracker 213-R can be configured to be in communication with the second computer workstation, for example, via a communications link. The second tracker can be configured to track, for example, via IR optical tracking, a location of a portion of the second cranial reference module. The communications link can connect the first computer workstation and the second computer workstation such that the first computer workstation and second computer workstation are able to communicate.

The recipient sub-system 200-R can further include a second fragment reference unit 201-R. The second tracker 213-R can further be configured to track a location of a portion of the second fragment unit.

The recipient sub-system 200-R can further include a second cutting guide 219-R for attaching to a preselected location of a recipient skeleton 208. The second tracker 213-R can further be configured to track a location of a portion of the second cutting guide.

Additionally, when a surgeon has removed the donor skeletal fragment from the donor, it can then be transferred for attachment onto the recipient. Accordingly, the second tracker 213-R can be further configured to track a location of a portion of the first cutting guide 207-D so that it can be matched relative a position of the second cranial reference module 205-R.

The first cranial reference unit, the second cranial reference unit, or both the first and second cranial reference units can include a kinematic mount 205 as described above.

Figure 3:
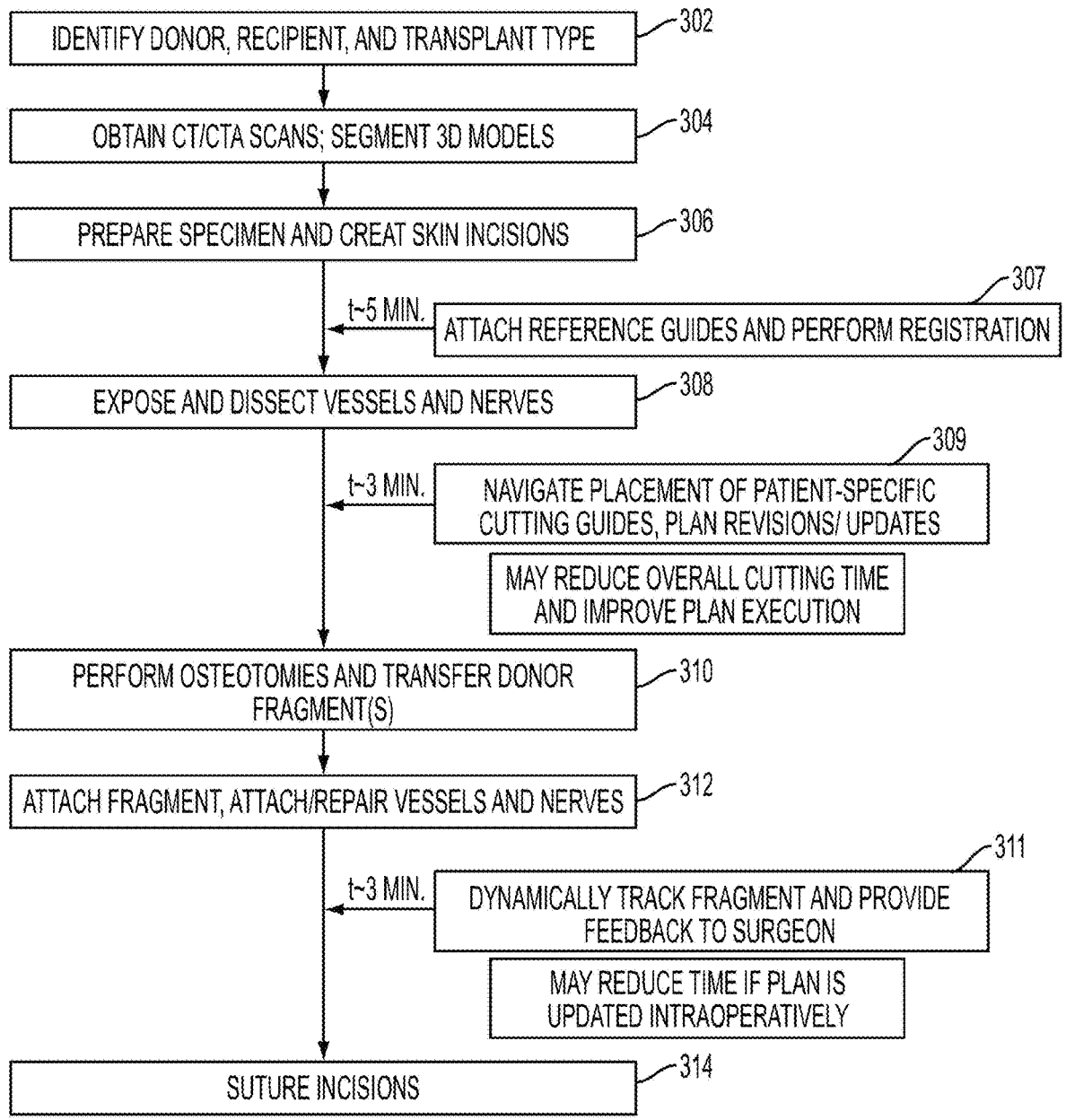
FIG. 3 is a flow chart depicting a procedure associated with use of the surgical system, for example, the surgical system of FIGS. 2A-2C.

Using the system of FIGS. 2A-2G, it is possible to execute a surgical method, such as the surgical method described in FIG. 3. For example, in step 302 a donor, recipient and transplant type are identified. CT/CTA scans of both the donor and recipient are collected and 3D models are created in step 304. The donor and recipients are prepared for surgery with the creation of skin incisions in step 306. The method continues at 307 with attachment of reference guides and performing registration. For example, a first cranial reference unit can be attached to a donor skeleton, a first fragment reference unit can also be attached to the donor skeleton at a location that is different that of the first cranial reference unit. The locations of the first cranial reference unit and the first fragment reference unit can be tracked with a first tracker. 3D reconstructions of the donor skeleton can be constructed showing a first virtual cranial reference unit and first virtual fragment reference unit superimposed on the first 3D reconstruction at locations that correspond to relative positions of the first cranial reference unit and the first fragment reference unit.

A second cranial reference unit can be attached to a recipient skeleton. A second location of the second cranial reference unit can be tracked with a second tracker. A second 3D reconstruction of the recipient skeleton can be created with a second virtual cranial reference unit superimposed on the second 3D reconstruction at a location that corresponds to a location of the second cranial reference unit. At 308, vessels and nerves are dissected and exposed. At this stage, navigation of the patient-specific cutting guides can occur, with plan revision and updates provided periodically. For example, a first cutting guide, such as a patient-specific cutting guide according to the descriptions provided above, can be attached onto the donor skeleton at a preselected location such as that corresponding to a planned cut-plane. The location of the first cutting guide can be tracked with the first tracker. A first virtual cutting guide can be superimposed on the first 3D reconstruction at a location that corresponds to a location of the first cutting guide relative to the location of the first cranial reference unit or the location of the first fragment reference unit.

A first virtual fragment can be formed by segmenting the 3D reconstruction of the donor skeleton at a location adjacent to the first virtual cutting guide. The first virtual fragment can be superimposed on the second 3D reconstruction of the recipient skeleton.

At step 310, a surgeon can perform an osteotomy on the donor skeleton to remove the first fragment by cutting the skeleton along a cutting path defined by the first cutting guide. Upon transferring the removed skeletal fragment from the donor, the first cutting guide can be tracked, by the second tracker, for example, when the fragment is brought near the recipient for attachment. The surgeon can then navigate placement of the cutting guide as it is dynamically tracked at step 311, and will receive feedback from the system such as by referring to a first virtual fragment that is superimposed on the second 3D reconstruction to form a hybrid 3D reconstruction. At step 312, the first fragment can then be attached to the recipient skeleton via known surgical methods and the incisions can be sutured in step 314.

The step of superimposing the first virtual fragment on the second 3D reconstruction of the recipient skeleton can include performing an automated cephalometric computation for the hybrid reconstruction. In fact, the step of superimposing the first virtual fragment on the second 3D reconstruction can include providing a communications link between a first workstation on which the first 3D reconstruction is displayed and a second workstation on which the second 3D reconstruction is displayed, and initiating a data transfer protocol that causes the first workstation and the second workstation to send electronic signals through the communications link.

Surgical methods of the embodiments described above can also include attaching a second cutting guide at a preselected location on the recipient skeleton. The second cutting guide can also include features of the cutting guide described above.

For the surgical methods of embodiments described herein the donor skeleton can include a male skeleton or a female skeleton and the recipient skeleton can include a female skeleton. Alternatively, the donor skeleton can include a male or female skeleton and the recipient skeleton can include a male skeleton.

Surgical methods of the embodiments can further include steps for assessing a size-mismatch between the donor skeleton and the recipient skeleton by measuring a dorsal maxillary interface between the first fragment and recipient skeleton. In an embodiment, the surgical method can include selecting a location of the first fragment onto the recipient skeleton that minimizes dorsal step-off deformity at the area of osteosynthesis. In an embodiment, the first cutting guide, the second cutting guide, or both the first cutting guide and the second guide may be or include concentric cutting guides.

Surgical methods of embodiments can further include mapping the vascular system on the facial anatomy of both the recipient and the donor and superimposing corresponding virtual representations of the vascular system and the facial anatomy onto the first 3D representation, such as shown in FIG. 4B Surgical methods of embodiments can include a method for registration of a preoperative model, for example a model reconstructed from CT data, to donor and recipient anatomy. Such a method can include: creating a plurality of indentations on the donor skeleton, creating a plurality of virtual markers on the first 3D reconstruction of the donor skeleton corresponding to the locations of the indentations on the donor skeleton, placing a trackable object on at least one of the plurality of indentations, and determining whether a subsequent location of the virtual markers is within a predetermined tolerance relative to an actual subsequent location of the indentations.

EXAMPLES

Example 1

Figure 9A:
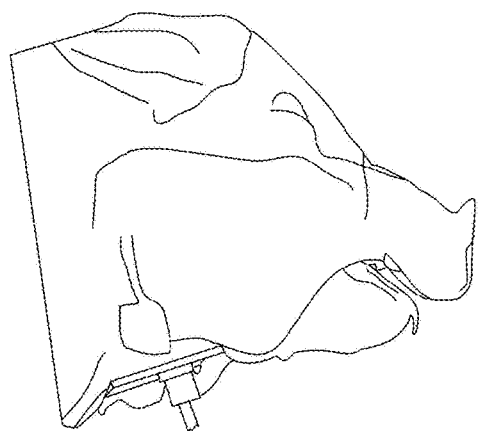
FIGS. 9A-9D are renderings showing exemplary surgical results.
Figure 9B:
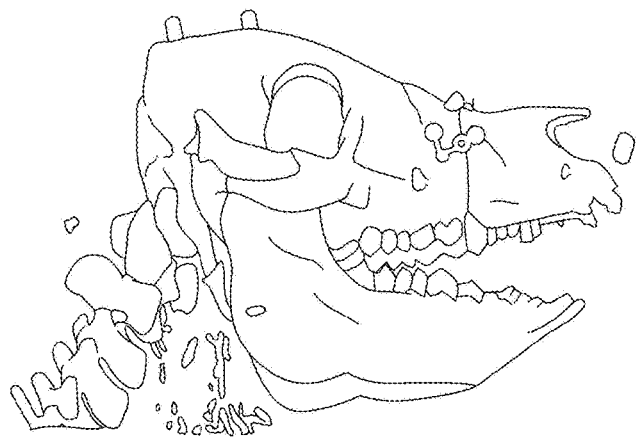
Figure 9C:
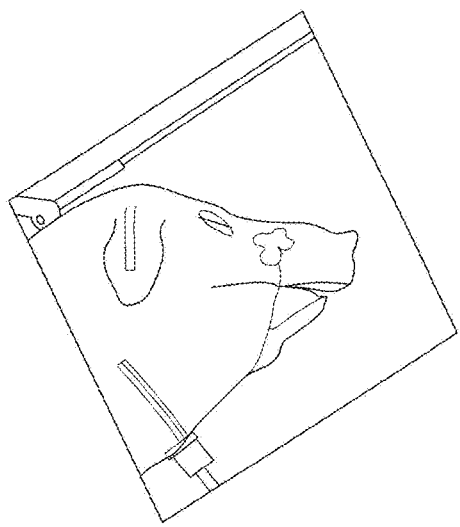
Figure 9D:
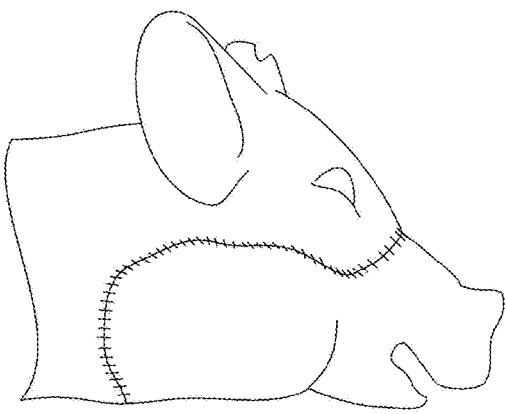

Live transplant surgeries (n=2) between four size-mismatched swine investigated whether or not an embodiment could actually assist a surgical team in planning and executing a desired surgical plan. As shown in FIGS. 9A-9B, the first live surgery confirmed the proposed utility of overcoming soft and hard tissue discrepancies related to function and aesthetics. The final occlusal plane within the first recipient was ideal and consistent with the virtual plan as seen on lateral cephalogram as shown in FIG. 10C. Pre-operative functional predictions of donor-to-recipient occlusion were realized based on cephalometric analyses as shown in FIG. 9C performed both before and after surgery. Soft tissue inconsistencies of the larger-to-smaller swine scenario were also reduced following the predicted movements of face, jaw and teeth as shown in FIG. 10D.

The second live surgery showed improved success as compared to its predecessor due to surgeon familiarity and technology modifications. System improvements and growing comfort of the surgeons led to reduced operative times for both donor and recipient surgeries. Overall the surgical time reduced from over 14 hours to less than 8 hours due to improved surgical workflow and increased comfort with a system of an embodiment.

Based on the results obtained in the live and plastic bone surgeries, the functions associated with setting up a system of an embodiment (attaching references, performing registration, attaching cutting guides) adds about 11 minutes to the total length of surgery.

Figure 11A:
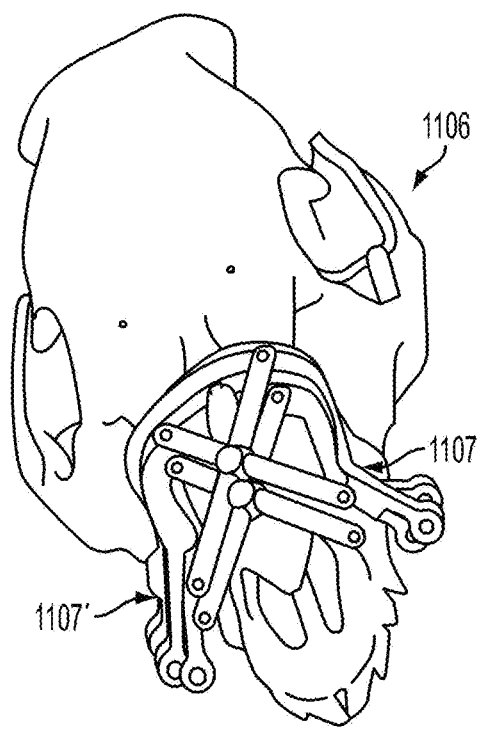
FIGS. 11A-11B are "on screen" images displayed by an imaging sub-system of a surgical system. The images depict an ideal location of a cutting guide versus an actual position and an actual inset position of a donor alloflap for aesthetic, dental, and skeletal relation in size-mismatched donors due to anterior translation of cutting guide.
Figure 11B:
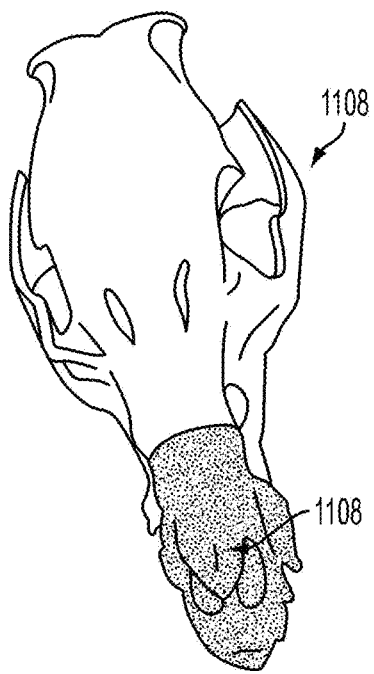
Figure 12A:
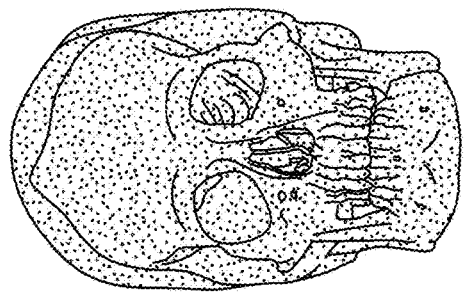
FIG. 12 illustrates a virtual osteotomy and planned cut plane placement on virtual representations of a skeletal feature.
Figure 12B:
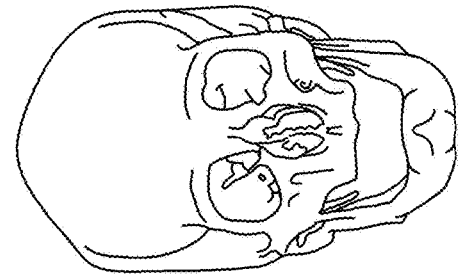
Figure 12C:
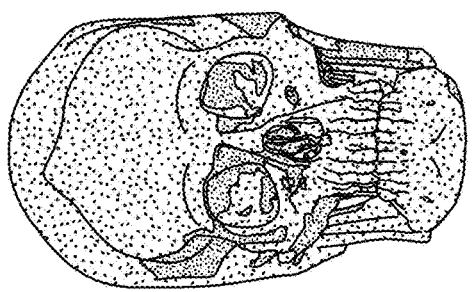
Figure 12D:
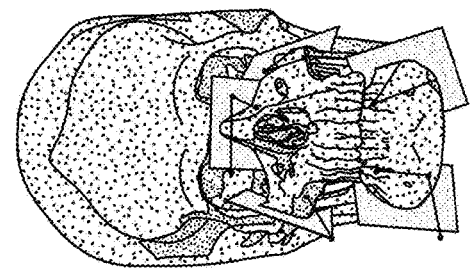
Figure 12E:
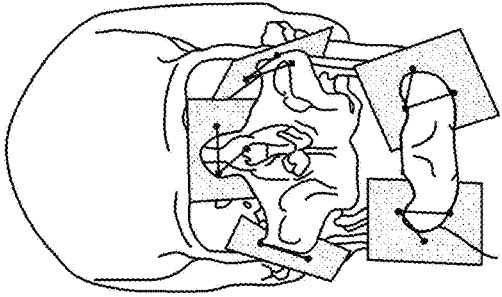
Figure 12F:
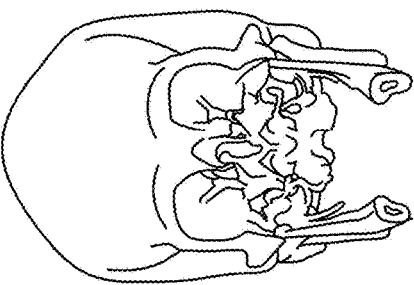
Figure 12G:
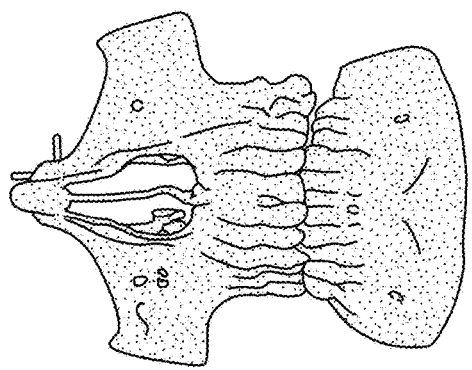
Figure 12H:
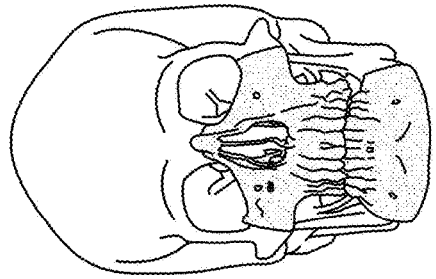
Figure 13A:
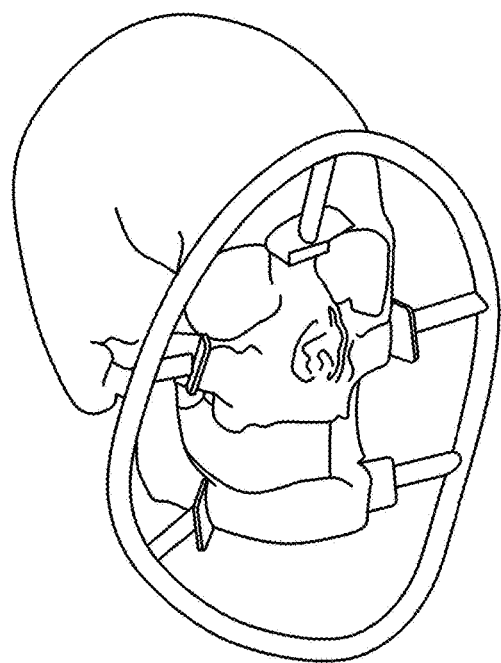
FIGS. 13A-13D illustrate a virtual placement of a cutting guide alongside (FIGS. 13A-13B) and illustrated representations of an actual placement (FIGS. 13C-13D).
Figure 13B:
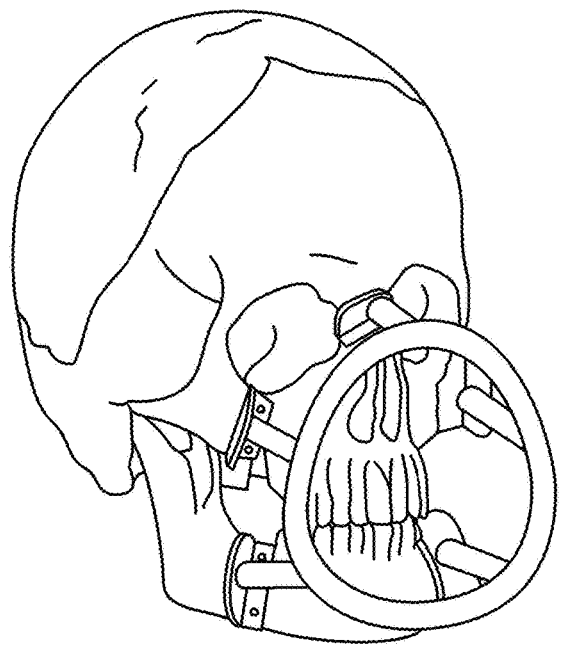
Figure 13C:
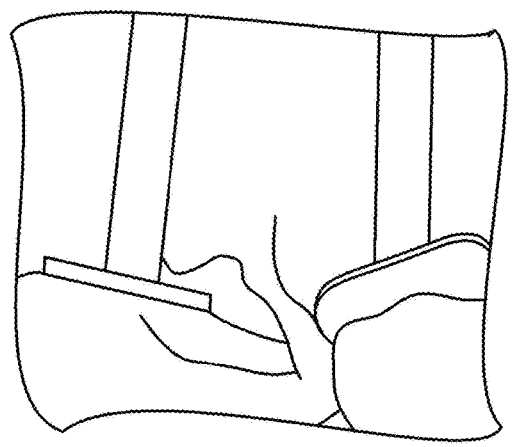
Figure 13D:
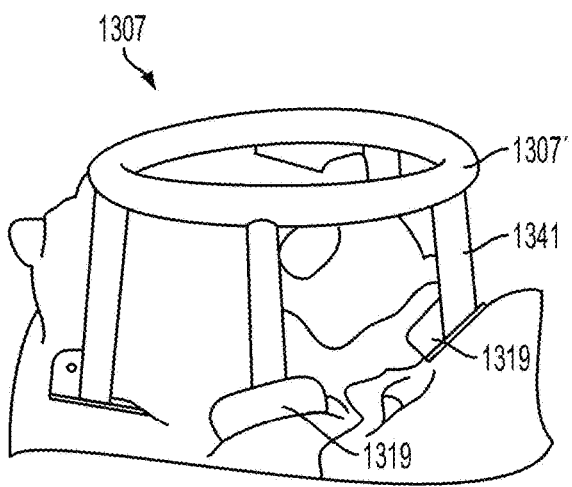

The system also recorded information, such as rendering information which can be stored in a storage medium of a workstation, relating the donor fragment 1002 to the recipient 1010 qualitatively as shown by color mismatch 1004, which matched the post-operative CT data as shown in FIG. 10. The recipient cutting guide 1107' was not placed as planned 1107 due to an unexpected collision between the cranial reference mount and the recipient cutting guide as shown in FIGS. 11A-11B. In this case, there was anterior translation of the cutting guide (toward the tip of the swine's snout) by approximately 4 cm.

Overall, the donor 1106 and recipient craniums (n=4) 1108 were registered successfully to the reference bodies for both live surgeries. The model to patient registration error across the surgeries was 0.6 (+/−0.24) mm. The cutting guide designs of the embodiments proved highly useful in carrying out the planned bone cuts, which compensated for size-mismatch discrepancies between donor and recipient. Marking spheres fixated to the guides allowed real-time movement tracking and "on-table" alloflap superimposition onto the recipient thereby allowing visualization of the final transplant result.

Example 2

Female and male donor heads (n=2), double-jaw, Le Fort III-based alloflaps were harvested using handheld osteotomes, a reciprocating saw, and a fine vibrating reciprocating saw. Both osteocutaneous alloflaps were harvested using a double-jaw, Le Fort III-based design (a craniomaxillofacial disjunction), with preservation of the pterygoid plates, incorporating all of the midfacial skeleton, complete anterior mandible with dentition, and overlying soft tissue components necessary for ideal reconstruction.

Prior to transplantation, both scenarios were completed virtually given the gender-specific challenges to allow custom guide fabrication as shown in panels A-H of FIG. 12. Once assimilated, the donor orthognathic two-jaw units were placed into external maxilla-mandibular fixation (MMF) using screw-fixated cutting guides to retain occlusal relationships during the mock transplants as shown in panels A-D of FIG. 13.

Figure 14A:
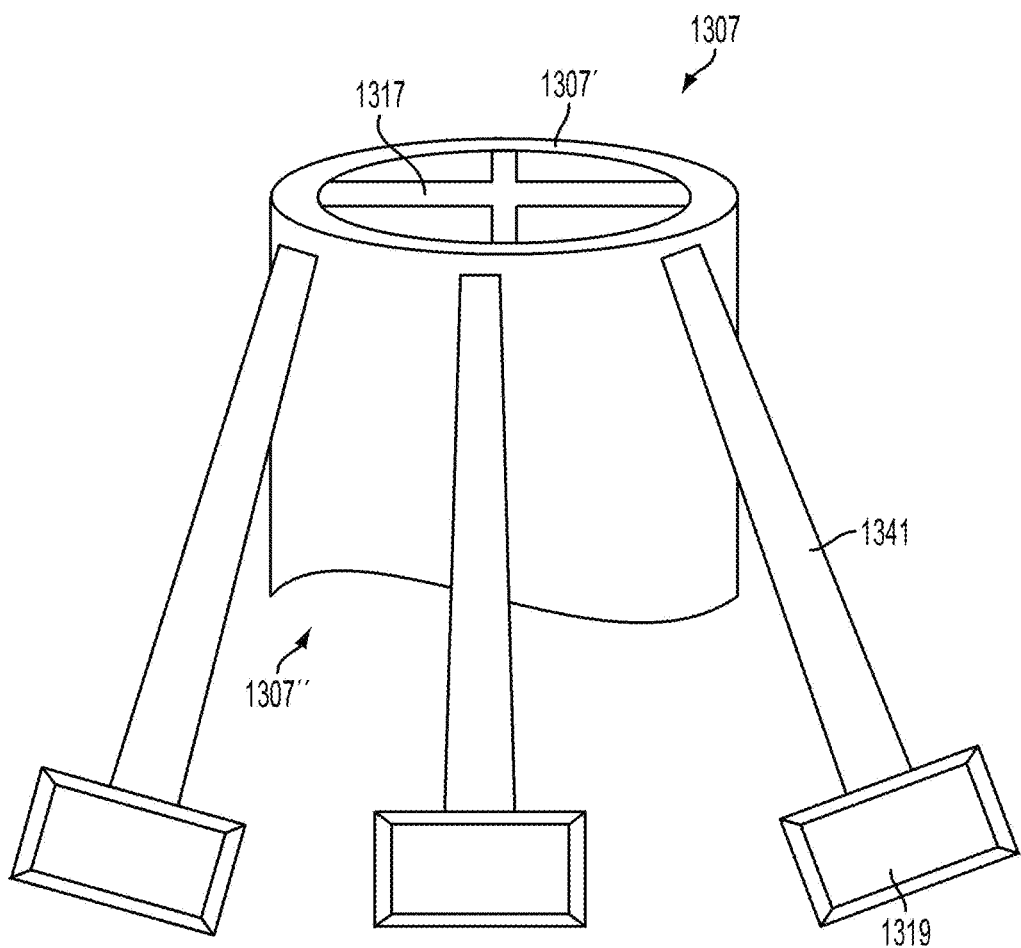
FIG. 14A illustrates a perspective view of a variation of a cutting guide, for example, a variation of the cutting guide of FIG. 13.
Figure 14B:
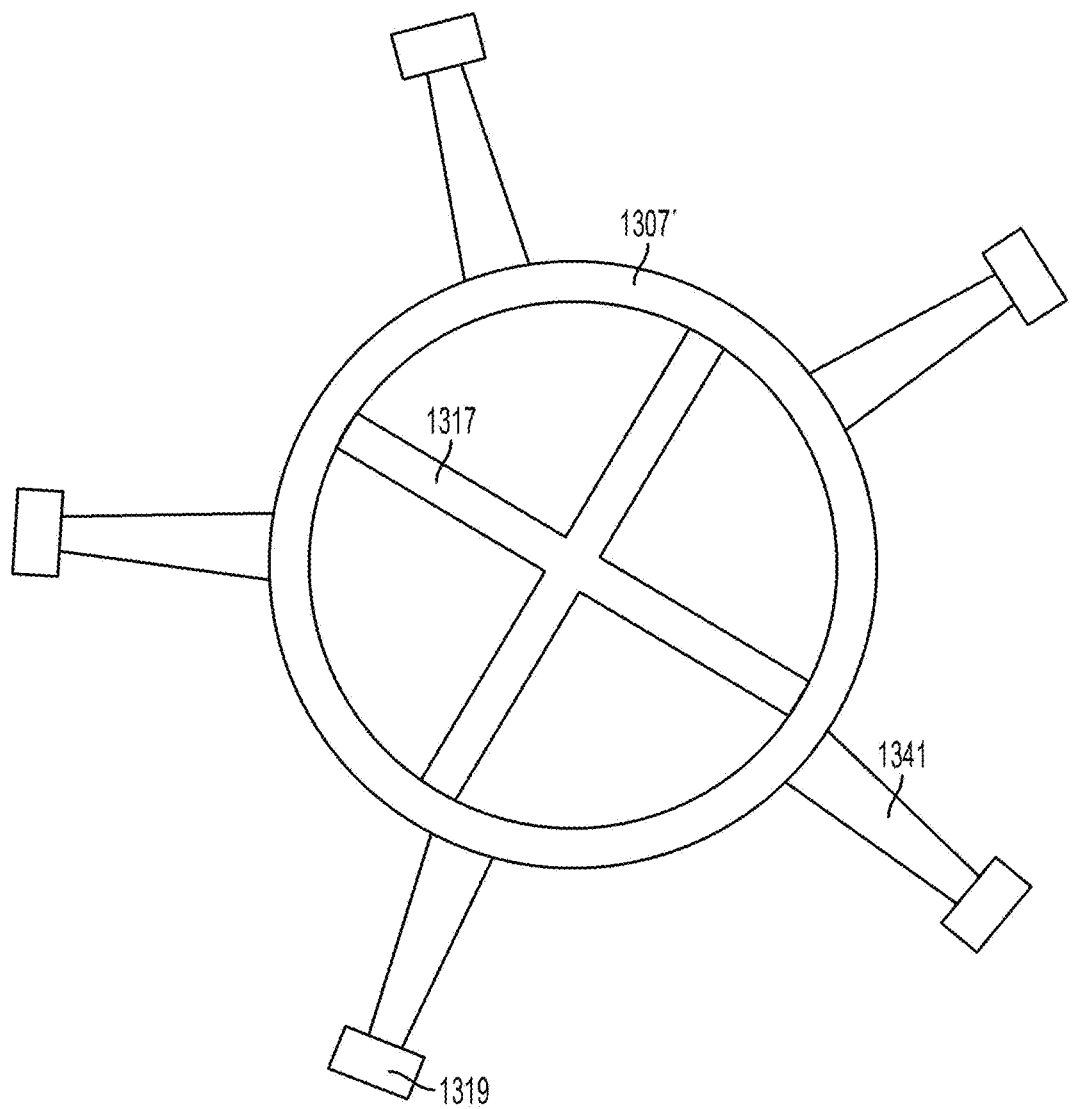
FIG. 14B illustrates a top view of a variation of a cutting guide, for example, a variation of the cutting guide of FIG. 13.

As shown in FIGS. 13, 14A-14B, an embodiment of a cutting guide 1307 can include a frame 1307' with at least one attachment surface 1319, for example 1 to 6 attachment surfaces, configured for attaching the cutting guide to a skeletal feature. The cutting guide can include a navigation surface 1317 (not shown in FIG. 13) connected to the frame. The navigation surface can include a reference geometry that can be tracked by a tracker, for example, via IR optical tracking. The at least one attachment surface 1319 can include a contoured surface corresponding to contours of portions of the skeletal feature, for example, such as the contours of a skeletal feature that intersect a planned-cut plane as indicated by 1319' in FIG. 12. The at least one attachment surface 1319 can be detachably connected to a skeletal feature. The at least one attachment surface 1319 can be detachably connected to an attachment guide 1341.

The attachment guide 1341 can be detachably connected to a portion of the frame 1307'. For example, attachment guides 1341 can be detachably connected via slots integrated into frame 1307', or held in place against frame 1307 with screws or the like. In another embodiment, attachment guides 1341 are formed as portions of frame 1307' but can be removed. The frame can have a ring-like shape (as shown in FIG. 13) or can have a cylinder-like shape (as shown in FIG. 14A). Frame 1307' having a cylinder like shape can have a bottom surface 1307" that rests against a patient's soft tissue to provide support for the frame.

For example, during a surgical procedure, 3D reconstructions of portions of a donor skeleton are created. Planned cutting planes are selected and a cutting guide with attachment surfaces having a contoured surface corresponding to contours of portions of the skeletal feature, for example, such as the contours of a skeletal feature that intersect a planned-cut plane, is designed. The designed cutting guide is manufactured via, for example, an additive manufacturing process. The designed cutting guide with an integrated navigation surface is attached to the patient. For example, the cutting guide can be designed such that it has a snap-on fit over the skeletal feature, which can be further secured to the skeletal feature with set screws. A surgeon removes a donor skeletal fragment with the cutting guide attached to the fragment. The donor skeletal fragment is then attached to the recipient. As the donor skeletal fragment is attached to the recipient, the attachment surfaces are removed from the donor fragment. For example, each of the attachment guides 1341 with a corresponding attachment surface 1319 can be detached from the frame 1307'. As this occurs, a cylindrical shaped frame 1307' has a bottom surface 1307" that rests against the soft tissue of the patient to provide stability for the remaining portions of the cutting guide and to hold the navigation surface 1317' in place.

While the invention has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. For example, the embodiments described herein can be used for navigation and modeling for osteotomy guidance during double-jaw face transplantation, single-jaw maxillofacial transplantation, and any other neurosurgical, ENT/head and neck surgery, or oral maxillofacial surgical procedure alike.

Embodiments described herein can include platforms for preoperative planning and intraoperative predictions related to soft tissue-skeletal-dental alignment with real-time tracking of cutting guides for two mismatched jaws of varying width, height and projection. Additional safeguards, such as collection of confidence points, further enable intraoperative verification of the system accuracy. This, in addition to performing real-time plan verification via tracking and dynamic cephalometry, can considerably increase the robustness of the systems described herein. Moreover, systems of embodiments can include a modular system that allows additional functionality to be continually added.

Embodiments described herein can include an approach for resolving conflicts in case of position discrepancies between the placement of the guide and the guide position prompted by the navigation software. Such discrepancy may be due to either the guide (soft tissue interference, iatrogenic malpositioning, changes since the CT data was obtained or imperfections in cutting guide construction/printing), and/or the navigation system (e.g. registration error, or unintended movement of the kinematic markers). To resolve these source(s) of discrepancy, four indentations can be created on a bone fragment (confidence points) where a reference kinematic marker is attached. At any time during an operation, a surgeon can use a digitizer and compare the consistency of the reported coordinates of the indentations via navigation to their coordinates with respect to a virtual computer model.

Embodiments described herein can include a system that provides real-time dynamic cephalometrics and/or biomechanical simulation for both planning and intraoperative guidance to ensure ideal outcomes in craniomaxillofacial surgery.

ADDITIONAL EMBODIMENTS

Osseointegrated Dental Implants

Patients with poor or missing dentitions may require dental implants to improve mastication. A popular modality with increasing indications includes "osseointegrated dental implants". Osseointegrated dental implants can include, and may consist of, a two-piece permanent implant device, which is placed into either the maxilla or mandible skeleton with a power drill for placement and stability. A second piece, in the shape of a tooth is screwed onto the secure base. An embodiment of the CAPE system described above can be used to provide the dentist or surgeon real-time cephalometric feedback in an effort to restore ideal occlusion and predict optimized mastication with biomechanical predictions—as similar to maxillofacial transplantation. As such, the dentist or surgeon placing these items needs to know the bone stock quality of the jaw(s) and angle to place the framework.

Osseointegrated Craniofacial Implants and Prosthetics

Patients with severe cranial or facial disfigurement may benefit from custom implant reconstruction or be poor surgical candidates due to overwhelming co-morbidities and/or because of an accompanying poor prognosis. Therefore, to help return these patients into society, some use craniofacial implants or prosthetics as a way to restore "normalcy". Application of these three-dimensional implants and prosthetics replacing absent craniofacial features (i.e., skeletal, nose, eye, etc) may either be hand-molded/painted by an anaplastologist or printed with 3D technology by a craniofacial technician. Either way, in an embodiment, the CAPE system described above can provide a one-stop solution for patients requiring alloplastic and/or bioengineered prosthetic reconstruction for large craniomaxillofacial deformities. The craniofacial implants can be tracked as similar to a donor face-jaw-teeth segment described above. For example, pre-placement images of the implant or prosthetic onlay may be fabricated, and surgical plans may be optimized since these appliances are placed with osseointegrated devices as similar to dental implants described above—with rigid plates and screws. As such, the surgeon placing them needs to know the exact location, underlying bone stock quality, and angle to place the framework, and desires unprecedented visual feedback as to the ideal position in three-dimensional space.

Craniomaxillofacial Trauma Reconstruction

Patients suffering from acute or chronic facial disfigurement are often seen by a craniomaxillofacial surgeon. Both penetrating and/or blunt trauma may cause significant damage to the underlying facial skeleton. As such, in an embodiment, the CAPE system technology described herein allows the surgeon to assess and optimize bone fragment reduction and reconstruction with real-time feedback. In addition, fractures affecting the jaws can be aided by real-time cephalometrics in hopes to restore the patient back to their pre-trauma angle/measurements (as a way to assure proper occlusion). Navigation, as described above in an embodiment of the CAPE system, can be exceptionally helpful for orbit fractures around the eye or cranial fractures around the brain, since the nerve anatomy is delicate and consistent—which makes it applicable to the CAPE system. In summary, a surgeon (including the likes of a Plastic surgeon, ENT surgeon, oral/OMFS surgeon, oculoplastic surgeon, neurosurgeon) reducing craniofacial fractures needs to know the bone stock quality remaining, where plates/screws are best placed, and the optimal plan prior to entering the operating room.

Neurosurgical Procedures

Neurosurgeons frequently perform delicate craniotomies for access for brain surgery. Currently, there are several navigational systems available. However, none of the conventional systems include features described in the embodiments of the CAPE platform as described above. That is, the conventional systems lack the ability to assist both pre-operatively with planning AND with intra-operative navigation for execution assistance. In addition, the current neurosurgery systems require the head to be placed in antiquated "bilateral skull clamp pins" during the entire surgery. This means that before each neurosurgery procedure starts, a big 3-piece clamp is crunched onto the skull of the patient to make sure the head does not move during surgery, particularly to allow for use of the conventional navigation systems. However, embodiments of the CAPE system, such as those described above, use a small, modified rigid cranial reference mount which removes the need for using a big, bulky clamp from the field and allows the surgeon to rotate the patient's head if and when needed. To a craniofacial plastic surgeon, who often is consulted to assist with simultaneous scalp reconstruction, elimination/removal of such pins from the surgical field is a huge advantage. For example, elimination of the pins makes scalp reconstruction in the setting of neurosurgery much safer since the pins aren't present to hold back mobilization and dissection of the nearby scalp, which is needed often for complex closure. It also, reduces the risk of surgical contamination since the current setup with pins is bulky and makes surgical draping and sterility much more difficult and awkward. A small cranial mount as part of the CAPE system is a huge advancement for the field.

Congenital Deformity Correction

Unfortunately, newborns are commonly born with craniofacial deformities to either maternal exposure or genetic abnormalities. As such, they may have major development problems with their skeleton and the overlying structures (eyes, ears, nose) may therefore appear abnormal. In addition, newborns may suffer from craniosynostosis (premature fusing of their cranial sutures) which causes major shifts in the shape of their head at birth. In an embodiment, the CAPE system described above, can be utilized to address such congenital deformities, irrespective of etiology. For example, if a 16 year old needs to have major Le Fort surgery to move the central facial skeleton into better position forward to improve breathing, mastication, and appearance, use of the CAPE system technology for both pre- and intra-operatively provides a huge advancement for the field.

Head/Neck and Facial Reconstruction (ENT Surgery)

Head and neck surgeons in the specialty of Otolarygology (ENT) are frequently reconstructing facial skeletons. Reasons include post-tumor resection, facial trauma, aesthetic improvement, congenital causes and/or functional improvement (nose, mouth, eyes, etc). Therefore, this specialty would greatly benefit from use of the CAPE system technology described herein. For example, in an embodiment, use of the CAPE system can be used in a wide range of surgeries including such instances as post-trauma fracture reduction/fixation, free tissue transfer planning and execution (i.e., free flap reconstruction with microsurgical fibula flaps for large bone defects where the leg bone receives dental implants for jaw reconstruction), smaller jaw reconstruction cases with implant materials, and/or anterior skull base reconstructions with neurosurgery following tumor resection. This specialty is very diverse, and therefore the CAPE system's easy adaptability can help make it greatly valuable to this group of surgeons.

Computer-Assisted Cranioplasty

At least some embodiments described herein can be used for the immediate surgical repair of large cranial defects (>5 $cm^2$). For example, embodiments described herein may be used for designing, forming and implanting customized craniofacial implants following benign/malignant skull neoplasm (tumor) resection (i.e. referred to as "single-stage implant cranioplasty"). Currently, it is challenging to reconstruct such patients with pre-fabricated implants using conventional methods since the actual size/shape of the defect site is unknown until the tumor is removed. Accordingly, use of a computer-assisted surgical system of an embodiment may significantly reduce the intraoperative time used for reshaping/resizing the customized implant. For example, embodiments provide visualization related to the tumor, the resulting skull defect, and the reshaped implant for exact positioning. In other words, in an embodiment, a Computer-Assisted Planning and Execution (CAPE) system that can be utilized for Le Fort-based, Face-Jaw-Teeth transplantation may also be used for improving both the pre-operative planning and intra-operative execution of single-stage implant cranioplasties. Cranioplasties may be performed to reconstruct large defects following stroke, trauma, aneurysmal bleeding, bone flap removal for infection, and oncological ablation. However, oncological defects are commonly reconstructed with "off-the-shelf" materials, as opposed to using a pre-fabricated customized implant—simply because the exact defect size/shape is unknown. With this in mind, embodiments described herein include a computer-assisted algorithm that may allow surgeons to reconstruct tumor defects with pre-customized cranial implants (CCIs) for an ideal result.

Nearly 250,000 primary brain tumors/skull-based neoplasms are diagnosed each year resulting in a range of 4500-5000 second-stage implant cranioplasties/year. Unfortunately, the common tumor defect cranioplasty is reconstructed with on-table manipulation of titanium mesh, liquid polymethylmethacrylate (PMMA), liquid hydroxyapatitie/bone cement (HA) or autologous split-thickness calvarial bone grafts (ref), which forces the surgeon to shape/mold these materials to an approximate size/shape. Expectingly, this results in some form of craniofacial asymmetry and a post-operative appearance which is suboptimal. Furthermore, the difficult shaping process may take several hours—which in turn increases anesthesia, total blood loss, risk for infection, morbidity, and all costs associated with longer operative times. Therefore, there is significant opportunity to extend this CAPE to thousands of patients.

In 2002, the advent of computer-aided design and manufacturing (CAD/CAM) was used for the first time to pre-emptively match the contralateral, non-operated skull for ideal contour and appearance, which provided for the use of CCIs. However, cranioplasties with such CCIs can only be performed as "second stage" operations during which a clinician, such as a surgeon, ensures that the CCI fits perfectly into the skull defect. Recent developments have demonstrated the feasibility of CCIs for "single-stage cranioplasty", but this involves using a handheld bur to shave down the pre-fabricated implant artistically. However, challenges in both assessing and predicting each tumor-resection deformity pre-surgery still limits the applicability of CCIs in this patient population. For example, challenges such as 1) unknown exact tumor size, 2) unknown growth from time of pre-op CT scan-to-actual day of surgery, and 3) the unknown resection margins needed to minimize local recurrence. For these cases, the CCI would need to be reshaped/resized intraoperatively from a size slightly larger than expected—which is a process that may take several (2-4) hours. However, there are no established planning and execution systems available to assist these single-stage reconstructions. Accordingly, embodiments described herein may be used by surgeons in performing single-stage cranioplasty following oncological resection. In other words, embodiments include algorithms for real-time updates related to single-stage customized implant cranioplasty. For example, in an embodiment, there is a Computer-Assisted Planning and Execution (CAPE) system, which is a SINGLE, seamless platform capable of being used for both planning (pre-op use) and navigation (intra-op use) which overcomes the limitations of conventional systems that do either one or the other. In addition, embodiments include novel hardware such as trackable cutting guides and rigid cranial reference mount.

Orthognathic Surgery

Orthognathic surgery describes any of surgical procedure type moving the jaw and/or jaw-teeth segments. This is most commonly performed by either oral surgeons, oral-maxillofacial surgeons (OMFS), or plastic surgeons. It is done currently both in the hospital as an insurance case or in the outpatient setting for a fee-for-service. It may be indicated for enhanced mastication, improved aesthetics, and/or both reasons. Having the ability to plan and predict jaw movements based on biomechanical muscle (i.e., external) forces will be immensely valuable to this field. In an embodiment, surgeons can utilize the CAPE system described above to predict functional jaw movements both at time of surgery and after surgery (1, 5, 10, 20 years post-op). In addition, in an embodiment, a surgeon can utilize the CAPE system to provide real-time cephalometric feedback, which provides an advancement not seen in the conventional systems. In comparison, for the last several centuries, oral surgeons have used splints fabricated in the dental lab pre-operatively for assistance in the operating room to help confirm dental alignment as planned. This takes time (e.g., 4-6 hours to make by hand), effort, and money. In contrast to the conventional systems, surgeons utilizing the CAPE system can go to the operating room with pre-fabricated cutting guides and tracking instruments, cut the jaws where planned, and then match the teeth on the table based on real-time cephalometric feedback and biomechanical jaw simulation to predict post-operative mastication—unlike ever before. For example, use of the CAPE system will allow surgeons to know instantaneously if the aesthetic and functional angles/ measurements are ideal and where they should be. In addition, the CAPE system is able to supply palatal cutting guides and pre-bent metal fixation plates (as opposed to the conventional methods that require hand bending each plate for proper shape). In summary, the CAPE system will be a "game-changer" for orthognathic surgery.

Orthognathic Biomechanical Simulation

Many types of surgery may benefit from intra-operative biomechanical simulation as described here following surgical intervention, including those fields of craniomaxillofacial surgery and orthopedic surgery—where both specialties transpose bones and structural tissues to new positions during surgery. Complex craniomaxillofacial surgery, particularly face-jaw-teeth transplantation or implantation of custom implants, includes replacing damaged portions of a recipient's face and underlying skeleton with either hard and soft tissues from the patient himself or herself or a cadaveric donor (transplantation), an osseointegrative implant (implantation), or a tissue engineered construct. Such surgeries have yielded sub-optimal results and a need for subsequent revision surgery due to patient mastication problems. For example, the post-surgical relationship between upper and lower jaws may be different than that of the healthy recipient. The new occlusal plane angle, dento-facial relationships, and muscle insertions directly affect the way muscles are recruited for providing forces and motions for chewing or biting. Such positioning parameters are difficult to determine before or during surgery.

Embodiments thus provide computer-assisted modeling and functional prediction for use before or during surgical intervention. Surgeries performed in concert with some embodiments may include one or both of pre-operative planning and intra-operative assessment. Such planning and/or assessment may include determining changes related to masticatory muscles affecting lower and/or upper jaws. In particular, some embodiments utilize patient-specific models, which can provide for surgical pre-operative planning and intra-operative assessment with the salient features of the outcome in mind. A variety of different positioning parameters that may be considered to obtain a positive outcome for this type of surgery, including muscle insertion locations and size matching between recipient skeletal features and the implant/transplant. More generally, embodiments may be used to assess and improve aesthetics, cephalometric measures in relation to implant/donor-to-recipient discrepancies, and optimum teeth occlusion. Note that the term "donor" as used herein may refer to a donor separate from the patient, e.g., a cadaveric donor, or to the patient himself or herself when the skeletal fragment transplant is taken from the patient himself or herself.

Figure 15A:
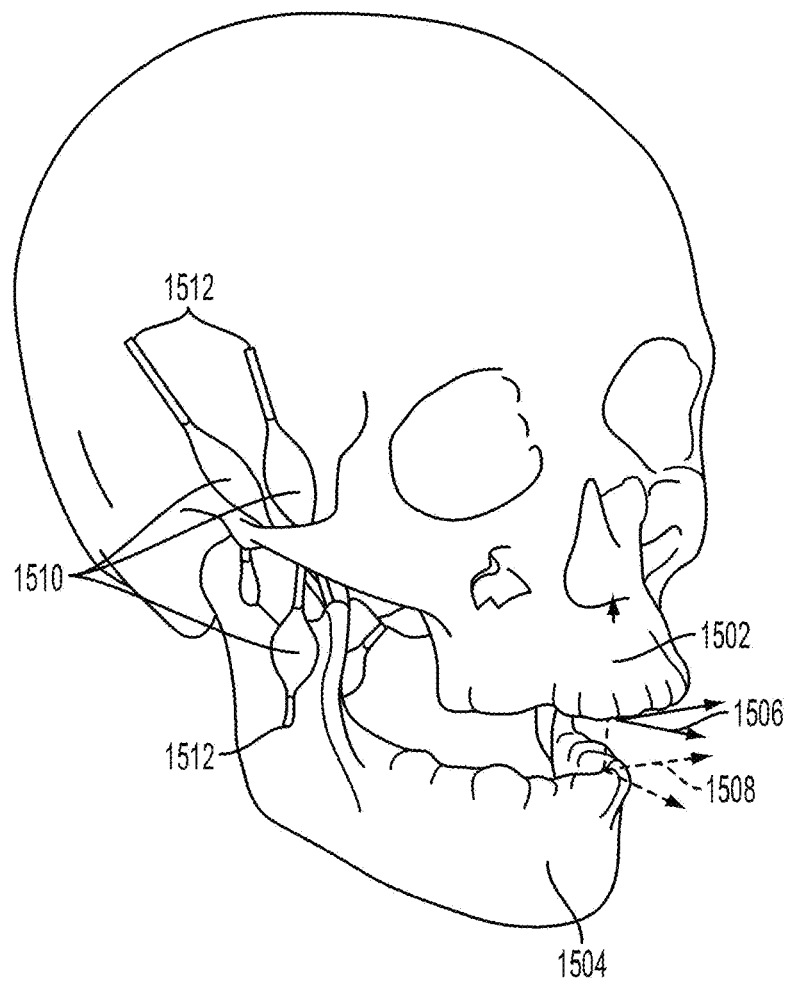
FIGS. 15A and 15B illustrate a biomechanical simulation of mastication of a recipient skull according to some embodiments.
Figure 15B:
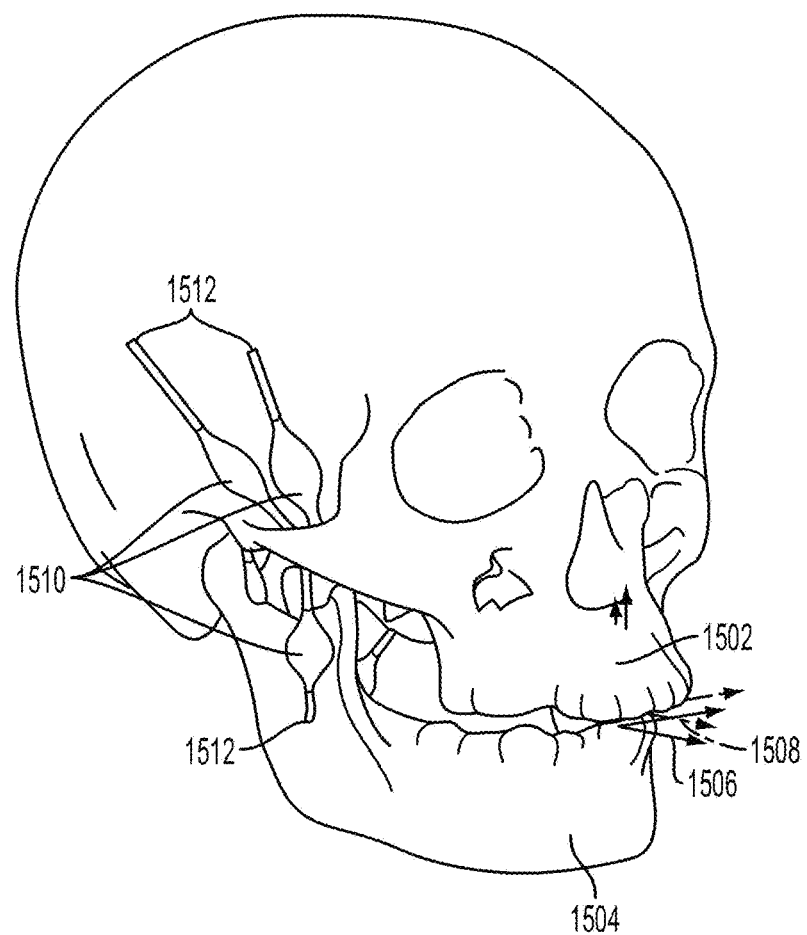

FIGS. 15A and 15B illustrate a biomechanical simulation of mastication in a patient skull according to some embodiments. That is, FIGS. 15A and 15B depict time slices, e.g., frames, from an animated mastication simulation. The simulation depicted in FIGS. 15A and 15B may be generated by, or by using, an embodiment. More particularly, an embodiment may accept patient-specific data and model mastication of a patient. The modeled mastication may be displayed on a computer monitor, for example. Suitable software for executing the simulation includes, e.g., THE ANYBODY MODELING SYSTEM, available from AnyBody Technology A/S, of Aalborg Øst, Denmark. FIGS. 15A and 15B depict still images from a displayed example mastication simulation. The simulation of FIGS. 15A and 15B may be used to obtain a baseline mastication simulation for a patient. The baseline mastication simulation may be compared to the simulation shown and described in reference to FIGS. 16A and 16B. In some embodiments, the baseline simulation is omitted.

Thus, FIGS. 15A and 15B depict three-dimensional computer-readable representations of maxilla 1502, mandible 1504, and coordinate axes 1506, 1508 associated therewith. The data used to represent maxilla 1502 and mandible 1504 may be obtained using a computed tomography (CT) scan, e.g., a cone beam computed tomography scan, or a magnetic resonance imaging scan, for example. The data may be stored in electronic persistent memory. As depicted in FIGS. 15A and 15B, maxilla 1502 is associated with coordinate axis 1506, and mandible 1504 is associated with coordinate axis 1508. Each axis 1504, 1506 is virtually attached to its respective three-dimensional representation and used to provide precise virtual positioning.

Also depicted in FIGS. 15A and 15B are virtual muscles 1510 and their respective insertion locations 1512. Generally, virtual muscles 1510 may be modeled as Hill-type actuators. Each virtual muscle 1510 may be modeled using estimated optimum fiber length and estimated force at optimum fiber length, for example. Fiber/tendon ratios may be estimated, with a portion of the total muscle length at jaw close considered optimum fiber length and the remaining portion as slack tendon length. At a portion of tension (e.g., 5%), each muscle's tendon may be considered to provide a passive force equal to the maximum isometric fiber force. In the recipient simulation of FIG. 15A, attachment sites of virtual muscles 1510 may be determined based on imaging techniques and/or anatomical landmarks. Alternately, or in addition, inverse dynamic human masticatory biomechanics solvers, discussed immediately below, may provide optimized muscle insertion locations.

In general, inverse dynamic human masticatory biomechanics may be used to gather virtual muscle parameters. For such inverse problems, mandibular motion and temporomandibular joint reaction forces may be measured or otherwise empirically determined, and muscle activations or forces may be derived, e.g., estimated, therefrom. Various compute-implemented solvers may be utilized to that end. For example, two groups of suitable such solvers include forward dynamics-assisted and static optimizers. In the former, a set of initial muscle activations may be used for solving the forward dynamics problem and the resulting motion and/or external forces may be compared with the reference data. An optimizer may then adjust the muscle patterns so that the error is minimized. In the latter, at each simulation time step, an optimization problem may be solved that, based on muscle efforts, minimizes a (physiologically-related) function. Condylar joint load or muscle fatigue are among the possible such objective functions. This approach is computationally inexpensive and can be used for various sensitivity analyses including optimizing muscle attachment sites. Another possible technique of optimization in masticatory dynamics is the method of dynamic geometric optimization, where muscles are virtually activated based on their lines of action with respect to a specific tracked target point on a mandible.

As shown in FIG. 15A, the simulation provides an open-jaw representation. Activating virtual muscles 1510 causes the jaw to close as depicted in FIG. 15B, thus simulating mastication. The simulated mastication of FIGS. 15A and 15B may be compared to the simulated mastication of FIGS. 16A and 16B, toward assessing whether proposed pre-surgical position parameters, or in-use intra-surgery positioning parameters, are likely to provide an acceptable outcome.

Figure 16A:
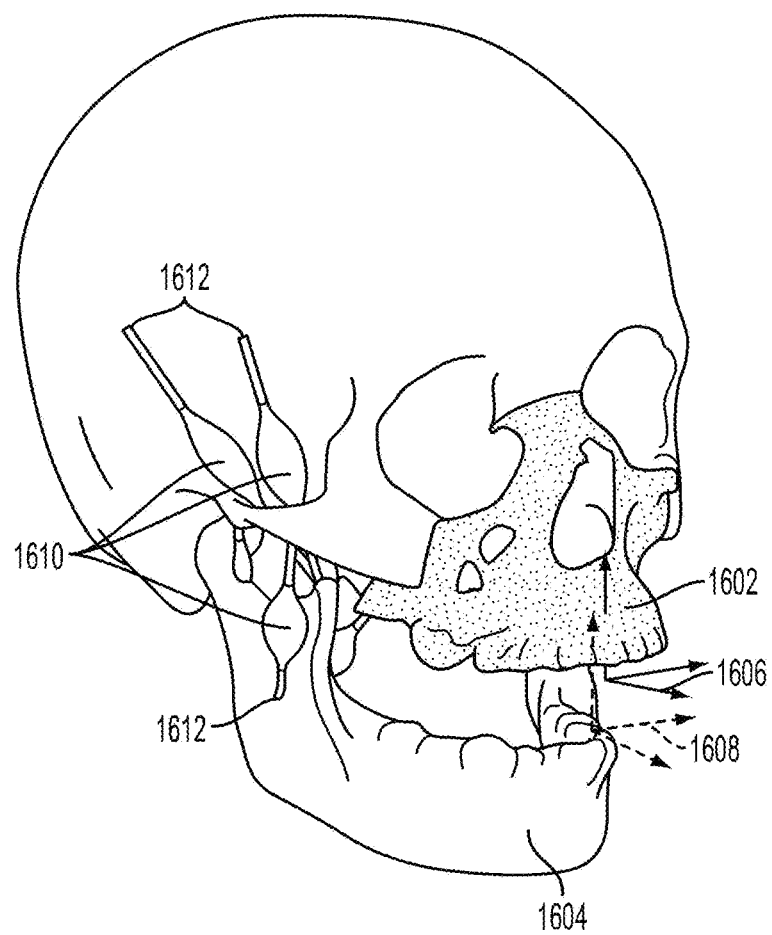
FIGS. 16A and 16B illustrate a biomechanical simulation of mastication of a hybrid skull according to some embodiments.
Figure 16B:
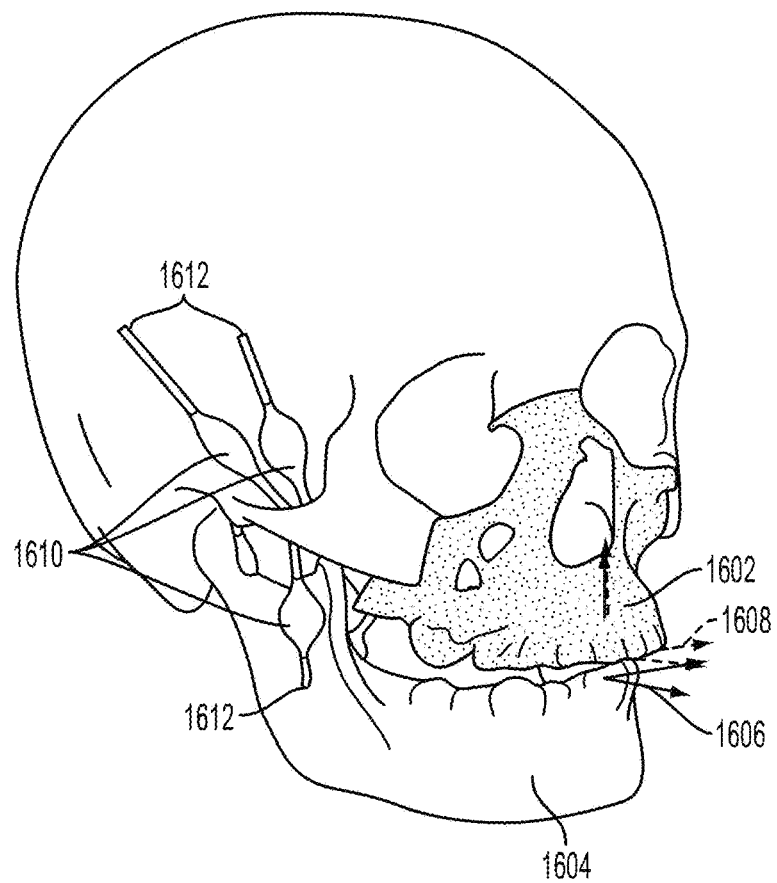

FIGS. 16A and 16B illustrate a biomechanical simulation of mastication of a hybrid craniomsaxillofacial skeleton according to some embodiments. In particular, FIGS. 16A and 16B are still images (e.g., time slices or frames) from an animated hybrid skull mastication simulation. In general, the hybrid may include a recipient portion of a mandible and/or a maxilla, as well as a portion of a donor or implant mandible or maxilla. Without loss of generality, FIGS. 16A and 16B depict a recipient mandible 1604, and a donor or implant maxilla 1606. The simulation shown and discussed in reference to FIGS. 16A and 16B may be used to assess whether an acceptable outcome is likely with the simulated set of positioning parameters.

The simulation of FIGS. 16A and 16B may be used to evaluate positioning parameters for suitability in producing an acceptable outcome. Positioning parameters suitable for evaluation using the simulation include fragment relative positioning and muscle insertion locations. Toward assessing whether the simulation represents an acceptable outcome, the physician may assess whether the simulation includes adequate teeth alignment, whether the fragments are suitably matched in terms of size, whether the muscle attachment sites should be adjusted, whether the fragment sizes match (between recipient and donor/implant), whether the teeth occlusion is acceptable, whether the aesthetics are acceptable, etc. A physician may view a display of the animated simulation and assess whether the positioning parameters of the simulation would be suitable in the patient. Such a physician may view the simulated surgery and its affect on function before surgery for preoperative planning purposes. Alternately, or in addition, the physician my view the simulation predictions during surgery following surgical manipulation in order to reassess initial positioning parameter choices or assess revised positioning parameters, for example. A physician may conclude, using the simulation, that one or more such parameters should be adjusted. The physician may repeat the simulation with the adjusted parameters, and use related information provided by the CAPE system.

Thus, FIGS. 16A and 16B depict computer-displayed representations of maxilla 1602, mandible 1604, and coordinate axes 1606, 1608 associated therewith. The data used to represent maxilla 1602 and mandible 1604 may be obtained using a computed tomography (CT) scan, e.g., a cone beam computed tomography scan, or a magnetic resonance imaging scan, for example, and stored in persistent electronic memory. Maxilla 1602 is associated with coordinate axis 1606, and mandible 1604 is associated with coordinate axis 1608. Each axis 1604, 1606, is virtually attached to its respective three-dimensional representation and used to provide precise positioning. Axes 1604, 1606 may be hidden in some embodiments.

Also depicted in FIGS. 16A and 16B are virtual muscles 1610 and their respective insertion locations 1612. As discussed above in reference to FIGS. 15A and 15B, virtual muscles 1610 may be modeled as Hill-type actuators, with muscle parameters obtained by, for example, estimation using inverse dynamic human masticatory biomechanics as computed by computer-implemented solvers. Muscle parameters include, for example, estimated optimum fiber length, estimated force at optimum fiber length, and fiber/tendon ratios.

An open-jaw representation is depicted in FIG. 16A, with a corresponding closed-jaw simulation depicted in FIG. 16B. Activating virtual muscles 1610 causes the jaw to close, simulating mastication. The simulated mastication of FIGS. 16A and 16B may be used to assess whether proposed pre-surgical position parameters, or in-use intra-surgery positioning parameters, are likely to provide an acceptable outcome.

Figure 17:
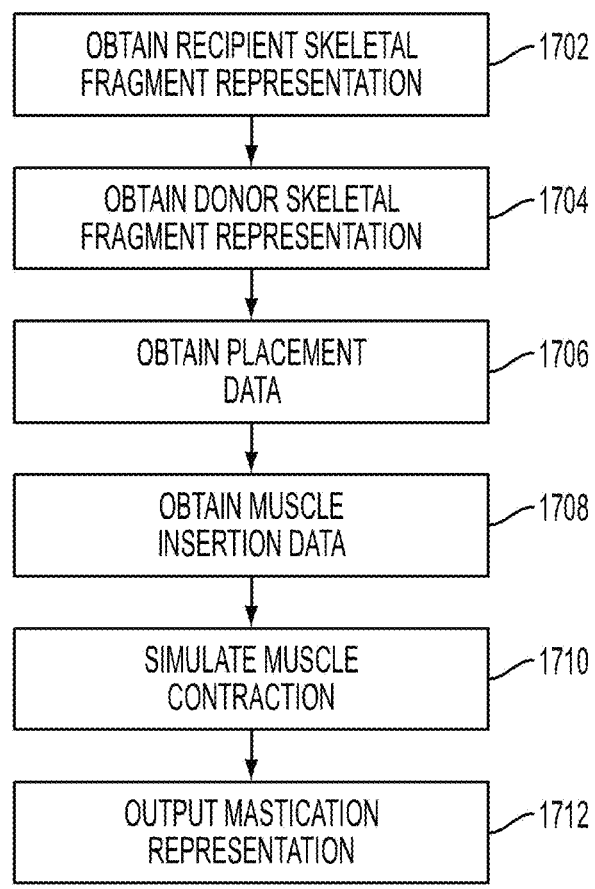
FIG. 17 is a workflow of a method according to various embodiments.

FIG. 17 is a workflow of a method according to various embodiments. The method of FIG. 17 may be implemented using electronic computing equipment, including, for example, a computed tomography scanner and a display device coupled to electronic processors configured to execute the steps of the method. The electronic processors may be communicatively coupled to one or more electronic memory devices, persistent or otherwise, that contain instructions which, when executed by the processors, implement the method. The method shown and described in reference to FIG. 17 may be used to produce simulations as shown and described herein in reference to FIGS. 15A, 15B, 16A and 16B.

At block 1702, the method obtains a computer-readable three-dimensional representation of a recipient skeletal fragment. The recipient skeletal fragment typically includes a portion of a mandible, a maxilla, or both. The representation may be generated using, e.g., a computed tomography (CT) scan, e.g., a cone beam computed tomography scan, or a magnetic resonance imaging scan, for example. The representation may be stored in volatile and/or persistent electronic memory. The method may obtain the representation by, e.g., retrieving it from memory, by receiving it over a network, or by generating it using an imaging device as described At block 1704, the method obtains a computer-readable three-dimensional representation of a donor skeletal fragment. This step refers to a donor skeletal fragment by way of non-limiting example; is some embodiments, an implant is used instead. Nevertheless, the present description refers to "donor skeletal fragment", with the understanding that this may be replaced by "implant" mutatis mutandis. The skeletal fragment typically includes a portion of a mandible, a maxilla, or both. The representation may be generated using a computed tomography (CT) scan such as a cone beam computed tomography scan, or a magnetic resonance imaging scan, for example. The representation may be stored in volatile and/or persistent electronic memory. The method may obtain the representation by, e.g., retrieving it from memory, by receiving it over a network, or by generating it using an imaging device as described.

At block 1706, the method obtains placement data representing a position of at least a portion of the donor skeletal fragment (respectively, implant) relative to at least a portion of the recipient skeletal fragment. The placement data may be in the form of, for example, data provided by a tracker as shown and discussed herein in reference to FIG. 2, for example. Alternately, or in addition, the placement data may be obtained from a physician using a user interface to virtually manipulate the representation of the donor skeletal fragment relative to the representation of the recipient skeletal fragment. In general, the placement data is with respect to all or part of the skeletal fragments for which representations were obtained, recognizing that one or both of the skeletal fragments may be modified by, e.g., reducing their size, before the positioning is attempted.

At block 1708, the method obtains muscle insertion data representing at least one muscle insertion location on the donor skeletal fragment (respectively, implant), the recipient skeletal fragment, or both. The data may be made relative to cephalometric landmarks as described herein. The data may be obtained from a physician using a user interface to virtually manipulate insertion locations of muscle representations relative to the representation of the donor skeletal fragment and the representation of the recipient skeletal fragment.

At block 1710, the method simulates contractions of one or a plurality of muscles positioned according to the muscle insertion data obtained at block 1708 in a representation of a surgical hybrid that includes at least a portion of the donor skeletal fragment positioned according to the placement data relative to at least a portion of the recipient skeletal fragment. Of note, this type of technology could be applicable to the entire human skeleton. The simulation may be performed as described above in reference to FIGS. 15A, 15B, 16A and 16B. In particular, the simulation may utilize estimated muscle parameters as described.

At block 1712, the method outputs a mastication representation represented by the simulation. That is, a result of the muscle contraction simulation is that the skeletal fragment representations move relative to each-other, thus simulating mastication. The output may be in the form of an animation, e.g., an animation such as that described in reference to FIGS. 16A and 16B above. That is, in some embodiments, the outputting comprises displaying. Alternately, or in addition, the output may be to a different process or system, e.g., configured to assess whether the simulated hybrid would be acceptable.

The terms "couple," "coupled," "connect," "connection," "connected," "in connection with," and "connecting" refer to "in direct connection with" or "in connection with via one or more intermediate elements or members." Furthermore, to the extent that the terms "including", "includes", "having", "has", "with", or variants thereof are used in either the detailed description and the claims, such terms are intended to be inclusive in a manner similar to the term "comprising." As used herein, the phrase "at least one of" or "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The steps in the methods described herein may be implemented by running one or more functional modules in an information-processing apparatus such as general purpose processors or application-specific chips, such as ASICs, FPGAs, PLDs, or other appropriate devices. These modules, combinations of these modules, and/or their combination with general hardware are all included within the scope of protection of the invention.

Certain embodiments can be performed as a computer program or set of programs. The computer programs can exist in a variety of forms both active and inactive. For example, the computer programs can exist as computer-readable media that include software program(s) comprised of program instructions in source code, object code, executable code or other formats, firmware program(s), or hardware description language (HDL) files. Any of the above can be embodied on a non-transitory computer readable medium, which includes storage devices, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

What is claimed is:

1. A method of simulating mastication, the method comprising:
    obtaining a computer-readable three-dimensional representation of a first skeletal fragment comprising a portion of at least one of a mandible and a maxilla;
    obtaining a computer readable three-dimensional representation of a recipient skeletal fragment comprising a portion of at least one of a mandible and a maxilla;
    positioning a tracker to track a position of at least a portion of the first skeletal fragment, wherein the tracker is configured to be in communication with a computer workstation via a communications link;
    obtaining from the tracker placement data representing a position of at least a portion of the first skeletal fragment relative to at least a portion of the recipient skeletal fragment, wherein the obtaining placement data comprises at least tracking a position of at least a portion of the first skeletal fragment during a surgery;
    obtaining cephalometric landmark locations during the surgery in real time based on the obtained tracker placement data, wherein the cephalometric landmark locations comprise one or more of: Gonion ("Go"), Nasion ("N"), A point ("A"), B point ("B"), Sella ("S"), Menton ("M"), left/right Zygoma ("ZY"), or Os occipital ("OCC");
    calculating, during surgery, an orientation value of the first skeletal fragment with respect to the recipient skeletal fragment based upon two of the obtained cephalometric landmark locations;
    outputting the determined orientation value in real time during the surgery;
    obtaining muscle insertion data representing at least one muscle insertion location on at least one of the first skeletal fragment and the recipient skeletal fragment;
    simulating a contraction of a muscle positioned according to the muscle insertion data in a representation of a surgical hybrid comprising at least a portion of the first skeletal fragment positioned according to the placement data relative to at least a portion of the recipient skeletal fragment; and
    outputting a representation of mastication represented by the simulating.

2. The method of claim 1, wherein the obtaining placement data comprises obtaining placement data prior to a surgery to transplant at least a portion of the first skeletal fragment into a recipient.

3. The method of claim 1, further comprising obtaining muscle activation data representing at least one muscle contraction, wherein the simulating comprises simulating a contraction of a muscle according to the muscle activation data.

4. A method of simulating mastication, the method comprising:
    obtaining a computer-readable three-dimensional representation of an osseointegrative implant comprising a portion of at least one of a mandible and a maxilla;
    obtaining a computer readable three-dimensional representation of a recipient skeletal fragment comprising a portion of at least one of a mandible and a maxilla;
    positioning a tracker to track a position of at least a portion of the osseointegrative implant, wherein the tracker is configured to be in communication with a computer workstation via a communications link;
    obtaining from the tracker placement data representing a position of at least a portion of the osseointegrative implant relative to at least a portion of the recipient skeletal fragment, wherein the obtaining placement data comprises at least obtaining placement data during a surgery to implant at least a portion of the osseointegrative implant into a recipient;
    obtaining cephalometric landmark locations during the surgery in real time based on the obtained tracker placement data, wherein the cephalometric landmark locations comprise one or more of: Gonion ("Go"), Nasion ("N"), A point ("A"), B point ("B"), Sella ("S"), Menton ("M"), left/right Zygoma ("ZY"), or Os occipital ("OCC");
    calculating, during surgery, an orientation value of the osseointegrative implant with respect to the recipient skeletal fragment based upon two of the obtained cephalometric landmark locations;
    outputting the determined orientation value in real time during the surgery;
    obtaining muscle insertion data representing at least one muscle insertion location on at least one of the osseointegrative implant and the recipient skeletal fragment;
    simulating a contraction of a muscle positioned according to the muscle insertion data in a representation of a surgical hybrid comprising at least a portion of the osseointegrative implant positioned according to the placement data relative to at least a portion of the recipient skeletal fragment; and
    outputting a representation of mastication represented by the simulating.

5. The method of claim 4, wherein the obtaining placement data comprises obtaining placement data prior to a surgery to implant at least a portion of the osseointegrative implant into a recipient.

6. The method of claim 4, further comprising obtaining muscle activation data representing at least one muscle contraction, wherein the simulating comprises simulating a contraction of a muscle according to the muscle activation data.

7. A system for simulating mastication, the system comprising at least one electronic memory and at least one electronic processor, the at least one electronic memory including instructions which, when executed by the at least one electronic processor, cause the at least one electronic processor to perform a method comprising:
    obtaining a computer-readable three-dimensional representation of a first skeletal fragment comprising a portion of at least one of a mandible and a maxilla;
    obtaining a computer readable three-dimensional representation of a recipient skeletal fragment comprising a portion of at least one of a mandible and a maxilla;
    positioning a tracker to track a position of at least a portion of the first skeletal fragment, wherein the tracker is configured to be in communication with a computer workstation via a communications link;
    obtaining from the tracker placement data representing a position of at least a portion of the first skeletal fragment relative to at least a portion of the recipient skeletal fragment, wherein the obtaining placement data comprises at least tracking a position of at least a portion of the first skeletal fragment during a surgery;
    obtaining cephalometric landmark locations during the surgery in real time based on the obtained tracker placement data, wherein the cephalometric landmark locations comprise one or more of: Gonion ("Go"), Nasion ("N"), A point ("A"), B point ("B"), Sella ("S"), Menton ("M"), left/right Zygoma ("ZY"), or Os occipital ("OCC");

calculating, during surgery, an orientation value of the first skeletal fragment with respect to the recipient skeletal fragment based upon two of the obtained cephalometric landmark locations;

outputting the determined orientation value in real time during the surgery;

obtaining muscle insertion data representing at least one muscle insertion location on at least one of the first skeletal fragment and the recipient skeletal fragment;

simulating a contraction of a muscle positioned according to the muscle insertion data in a representation of a surgical hybrid comprising at least a portion of the first skeletal fragment positioned according to the placement data relative to at least a portion of the recipient skeletal fragment; and outputting a representation of mastication represented by the simulating.

8. The system of claim 7, wherein the obtaining placement data comprises obtaining placement data during a surgery to transplant at least a portion of the first skeletal fragment into a recipient.

9. The system of claim 7, wherein the at least one electronic memory further comprises instructions which, when executed by the at least one electronic processor, further cause the at least one electronic processor to obtain muscle activation data representing at least one muscle contraction, wherein the simulating comprises simulating a contraction of a muscle according to the muscle activation data.

10. A system for simulating mastication, the system comprising at least one electronic memory and at least one electronic processor, the at least one electronic memory including instructions which, when executed by the at least one electronic processor, cause the at least one electronic processor to perform a method comprising:

obtaining a computer-readable three-dimensional representation of an osseointegrative implant comprising a portion of at least one of a mandible and a maxilla;

obtaining a computer readable three-dimensional representation of a recipient skeletal fragment comprising a portion of at least one of a mandible and a maxilla;

positioning a tracker to track a position of at least a portion of the first skeletal fragment, wherein the tracker is configured to be in communication with a computer workstation via a communications link;

obtaining from the tracker placement data representing a position of at least a portion of the osseointegrative implant relative to at least a portion of the recipient skeletal fragment, wherein the obtaining placement data comprises at least tracking a position of at least a portion of the osseointegrative implant during a surgery;

obtaining cephalometric landmark locations during the surgery in real time based on the obtained tracker placement data, wherein the cephalometric landmark locations comprise one or more of: Gonion ("Go"), Nasion ("N"), A point ("A"), B point ("B"), Sella ("S"), Menton ("M"), left/right Zygoma ("ZY"), or Os occipital ("OCC");

calculating, during surgery, an orientation value of the osseointegrative implant with respect to the recipient skeletal fragment based upon two of the obtained cephalometric landmark locations;

outputting the determined orientation value in real time during the surgery; obtaining muscle insertion data representing at least one muscle insertion location on at least one of the osseointegrative implant and the recipient skeletal fragment;

simulating a contraction of a muscle positioned according to the muscle insertion data in a representation of a surgical hybrid comprising at least a portion of the osseointegrative implant positioned according to the placement data relative to at least a portion of the recipient skeletal fragment; and outputting a representation of mastication represented by the simulating.

11. The system of claim 10, wherein the obtaining placement data comprises obtaining placement data prior to a surgery to implant at least a portion of the osseointegrative implant into a recipient.

12. The system of claim 10, wherein the at least one electronic memory further comprises instructions which, when executed by the at least one electronic processor, further cause the at least one electronic processor to obtain muscle activation data representing at least one muscle contraction, wherein the simulating comprises simulating a contraction of a muscle according to the muscle activation data.

* * * * *

UNITED STATES PATENT AND TRADEMARK OFFICE
CERTIFICATE OF CORRECTION

PATENT NO.         : 10,631,877 B2
APPLICATION NO.    : 15/100241
DATED              : April 28, 2020
INVENTOR(S)        : Ryan Murphy et al.

Page 1 of 1

It is certified that error appears in the above-identified patent and that said Letters Patent is hereby corrected as shown below:

In the Specification

Column 1, Line 17 should read:
This invention was made with government support under Grant Nos. TR000424 and TR001079 awarded by the National Institutes of Health (NIH). The government has certain rights in the invention.

Signed and Sealed this
Sixteenth Day of June, 2020

Andrei Iancu
*Director of the United States Patent and Trademark Office*